United States Patent [19]
Nicklas et al.

[11] Patent Number: 5,058,598
[45] Date of Patent: Oct. 22, 1991

[54] METHOD AND APPARATUS FOR SYNTHESIZING LEADS OF AN ELECTROCARDIOGRAM

[76] Inventors: John M. Nicklas, 2086 Mershon, Ann Arbor, Mich. 48103; Julie A. Scherer, 1681 Broadway, Apt. 401, Ann Arbor, Mich. 48105

[21] Appl. No.: 562,872

[22] Filed: Aug. 3, 1990

[51] Int. Cl.$^5$ .......................................... A61B 5/0428
[52] U.S. Cl. .............................. 128/699; 364/413.06
[58] Field of Search ............... 128/696, 699, 702, 709; 364/413.06

[56] References Cited

U.S. PATENT DOCUMENTS

| | | | |
|---|---|---|---|
| 3,186,403 | 6/1965 | Bassett | 128/709 |
| 3,884,221 | 5/1975 | Eastman | 128/699 |
| 3,991,747 | 11/1976 | Stanly et al. | 128/709 |
| 4,697,597 | 10/1987 | Sanz et al. | 128/699 |
| 4,850,370 | 7/1989 | Dower | 128/699 |

OTHER PUBLICATIONS

Abildskov, J. A., M.D.; and Robert S. Wilkinson, Jr., M.D.; "The Relation of Precordial and Orthogonal Leads," *Circulation*, 28:58-63, Jan. 1963.
Burger, H. C., D.Sc., A. G. W. van Brummelen, Ph.D.; G. van Herpen, M.D., "Compromise in Vector Cardiography II. Alterations of Coefficients as a Means of Adapting One Lead System to Another," Dept. of Medical Physics, Physics Laboratory of Univ. Utrecht, Netherlands, pp. 666-678, Apr. 2, 1962.
Cady, L. D., Theresa Kwan, Fred Vogt, "Population Electrocardiographic Lead Transformations," *Progress in Biomedical Engineering*, pp. 151-158, Washington, D.C.; Spartan Books, 1967.
Cady, Jr., Lee D., Julian Isaacs, Theresa Kwan, and Fred Vogt, "Useful Components for Electrocardiographic Lead System Transformations," *Proc. XIth Intl. Vector Cardiographic Symposium*, pp. 72-77, May 15-17, 1970; North Holland Publ. Co., 1971.
Cady, L. D., Jr., F. B. Vogt, J. B. Vallhonrat, T. Kwan, "Routine Conversions of Frank Lead Displays to Standard Lead Cardiograms," *Proc. of the Long Island Jewish Hospital Symposium on Vector Cardiography*, pp. 15-18, North-Holland Publ. Co., May, 1965.
"Computed Relationship of Standard Electrocardiographic Leads," *Medical Research Engineering*, pp. 37-42, May-Jun. 1969.
Cowan, Marie J., and Robert A. Bruce, "Comparative Accuracy of Computerized Vectorcardiography, Polarcardiography, Aitoff Spatial Trajectory, Derived 12-Lead System, and Standard 12-Lead System for Detection of Myocardial Infarction," pp. 99-108.
Dower, Gordon E. et al., "Deriving the 12-Lead Electrocardiogram from Four (EASI) Electrodes," *Journal of Electrocardiology*, Supp. Issue, pp. S182-S187, 1988.
Dower, Gordon E., M.D., and Hilario Basto Machado, M.D., "XYZ Data Interpreted by a 12-Lead Computer Program Using the Derived Electrocardiogram," *J. Electrocardiology*, 12(3):249-61, 1979.
Dower, Gordon E., M.D.; "A Lead Synthesizer for the Frank System to Stimulate the Standard 12-Lead Electrocardiogram," *J. Electrocardiology*, 1(1):101-116, 1968.
Dower, Gordon E., M.D., "The ECGD: A Derivation of the ECG from VCG Leads," *J. Electrocardiology*, 17(2):189-92, 1984.
Dower, Gordon E., M.D. et al.; "On Deriving the Electrocardiogram from Vectorcardiographic Leads," *Clinical Cardiology*, 3:87-95, 1980.
Gaselowitz, David B., "On Modeling of the Electrocardiogram," pp. 259-264, Bioengineering Program, Pennsylvania State Univ., University Park, Pa.

(List continued on next page.)

*Primary Examiner*—William E. Kamm
*Attorney, Agent, or Firm*—Seed and Berry

[57] ABSTRACT

A method and apparatus for synthesizing data for an electrocardiographic lead is provided. In a preferred embodiment, the method and apparatus collect data from a set of base leads and a given lead. The method and apparatus generate transformation coefficients based on the collected data. The method and apparatus then collect additional data for the base leads, and apply the transformation coefficients to generate the synthesized data.

29 Claims, 21 Drawing Sheets

OTHER PUBLICATIONS

Horan, Leo G. et al., "Electrode Number and Body Surface Potential Map Reconstruction," Veterans Administration Medical Center, Hampton, Va., pp. 333-341.

McManus, Christopher D., M.A. et al., "Year to Year Variation of the Orthogonal Electrocardiogram and Vectorcardiogram Among 243 Normal White Males," *J. Electrocardiology*, 17(2):107-14, 1984.

Mizuno, Yasushi and Shoji Yasui, "The Relation of the Conventional Electrocardiogram to Orthogonal Leads—with Special Reference of Ventricular Hypertrophy," *Japanese Circulation Journal*, 31:1634-39, Nov., 1967.

Okada, Robert H., Ph.D. et al., "Synthesis of Precordial Potentials from the SVEC III Vectorcardiograph System," *Circulation Research* 7:185-91, Mar., 1959.

Pipberger, Hubert V., M.D. et al., "Correlation of Clinical Information in the Standard 12-Lead ECG and in a Corrected 3-Lead ECG," *American Heart Journal*, 61:34-43, May 18, 1960.

Plonsey, Robert, Ph.D., and Roger C. Barr, Ph.D., "Mathematical Modeling of Electrical Activity in the Heart," *J. Electrocardiology*, 20(3):219-26, 1987.

Scherer, J. A. et al., "Synthesis of the 12-Lead Electrocardiogram from a 3-Lead Semi-Orthogonal Subset Using Patient-Specific Linear Transformation Arrays," *Computer in Cardiology*, p. 72, 1988.

Wolk, H. K. et al., "Evaluation of Synthesized Standard Twelve-Leads and Frank Vector Leads," *Electrocardiology, Adv. Cardiology*, 16:87-97 (Karger, Basel, 1976).

METHOD AND APPARATUS FOR SYNTHESIZING LEADS OF AN ELECTROCARDIOGRAM

DESCRIPTION

1. Technical Field

This invention relates generally to a system for synthesizing leads of an electrocardiogram, and more specifically, to a method and an apparatus for synthesizing leads based on developing a patient-specific transform.

2. Background of the Invention

The electrocardiogram (ECG) is an important tool for monitoring heart activity and diagnosing heart conditions. The ECG is a recording of the electrical activity of the heart. This electrical activity causes the heart to contract. The contraction in turn causes blood to be pumped throughout the body. This electrical activity is spontaneously generated. As the cells within the heart, change from a negative potential to a positive potential (depolarization), the muscles within the heart contract. Conversely, when the cells change from a positive to a negative potential (repolarization), the muscles return to their non-contracted state. The periodic contraction of the heart causes the pumping action. This spontaneous electrical activity typically occurs about once a second. By analyzing a patient's ECG, various cardiac abnormalities, such as ischemia, can be detected.

The electrical activity of the heart can be monitored by electrodes placed on the surface of the body. As the cells depolarize and repolarize, the electrical potential on the surface of the body varies. Each contraction of the heart (heart beat) corresponds to one complete depolarization/repolarization cycle.

The standard ECG comprises twelve leads. A lead is the electrical potential (1) between two points on the body surface or (2) between one point and an average of multiple points. FIG. 6 shows a sample electrocardiogram displaying the twelve leads. The twelve leads are referred to as I, II, III, aVR, aVL, aVF, $V_1$, $V_2$, $V_3$, $V_4$, $V_5$, and $V_6$. The first six of the leads are known as limb leads, which are derived from three electrodes placed on the right arm, left arm, and left leg, as shown in FIG. 7. The fourth limb electrode, placed on the right leg, is a common ground for the entire system. Lead I is the potential difference between the left arm and the right arm. Lead II is the potential difference between the left leg and the right arm. Lead III is the potential difference between the left arm and the left leg. The other three limb leads—augmented voltage right arm (aVR), augmented voltage left arm (aVL), and augmented voltage left foot (aVF)—are the potential difference between their respective limb and the average potential of the other two limbs. FIG. 7 illustrates the measurement of aVR. The six limb leads are related mathematically. If any two of leads I, II, or III are given, then the other four limb leads can be calculated.

Leads $V_1$, $V_2$, $V_3$, $V_4$, $V_5$, and $V_6$ are known as chest leads. The electrodes for measuring these leads are positioned as shown in FIG. 8. These leads measure the potential difference between the electrodes and a common reference known as the Wilson Central Terminal. The Wilson Central Terminal is formed by connecting the electrodes on the right arm, left arm, and left leg through a resistor network to a common point.

To aid analysis, the ECG complex, which is the portion of the ECG associated with the electrical activity, is divided into three components: P wave, QRS complex, the T wave. The P wave corresponds to the depolarization of the atria, the QRS complex corresponds to the depolarization of the ventricles, and the T wave represents the repolarization of the ventricles. The repolarization of the atria occurs simultaneously with the depolarization of the ventricles, but is typically masked by the strong electrical signal generated by the ventricle depolarization.

In order to generate a twelve lead ECG, prior art techniques placed 10 electrodes on the patient as shown in FIGS. 7 and 8. However, placing so many electrodes is very time consuming. Also, electrodes have a tendency to move on the body's surface or to fall off the surface. Such electrode movement typically accompanies patient movement. The electrode movement results in incosistent ECG signals, which make patient diagnosis difficult. The use of ten electrodes and the ten wires is uncomfortable for a patient.

Consequently, only two electrodes are typically placed on a patient. Although the use of two electrodes is sufficient to monitor arrhythmia, it is insufficient to diagnosis problems such as ischemia. When an episode of silent ischemia occurs in a patient, then addition electrodes are attached so that the twelve lead ECG can be generated. However, because of the time needed to attach the additional electrodes, the episode of ischemia may be over by the time the twelve lead ECG is generated.

A further problem in generating the twelve lead ECG is that the placement of the electrodes at the standard positions may be difficult, if not impossible, due to a patient injury or suture. Thus, it is impossible to generate the standard twelve lead ECG for these patients.

Prior systems have attempted to synthesize the twelve lead ECG using fewer than the standard number of ten electrodes. However, all prior systems have produced unacceptable results. Some prior systems have attempted to synthesize the twelve lead ECG based on data gathered from orthogonal leads. An orthogonal lead system measures the electrical activity of the heart in an XYZ coordinate system. These prior orthogonal systems have produced unacceptable synthesized leads. Moreover, the use of orthogonal leads implies that electrodes are placed on a patient's chest and back. Such a placement of leads is uncomfortable for the patient. Some prior systems have attempted to provide a population-based synthesis. The population-based systems categorize patients based on several factors such as age, sex, body build, or electrical orientation of the heart. The systems then synthesize certain leads based on data gathered from other leads and patient category. These systems, however, have produced unacceptable results.

It is desirable to have a system that would produce an acceptable synthesis of the twelve lead ECG data gathered from less than ten electrodes. Furthermore, it is desirable to have a system that would produce an acceptable synthesis of a lead based on collecting of minimal amounts of actual lead data. It is desirable that such a system maximizes patient comfort.

SUMMARY OF THE INVENTION

It is an object of the present invention to provide a method and apparatus for synthesizing an ECG lead based on the actual data received for other leads.

It is another object of the present invention to provide a method and apparatus for generating a standard twelve lead ECG based on receiving data from three leads.

It is another object of the present invention to provide a method of segmenting the ECG complex to improve the methods of synthesizing lead data.

These and other objects, which will become apparent as the invention is more fully described below, are obtained by providing a method and apparatus for synthesizing lead data. In a preferred embodiment of the present invention, the method for synthesizing data for a given lead comprises the steps of selecting a plurality of base leads, gathering a first set of ECG data from the patient for the base leads and for the given lead for an interval corresponding to at least one ECG complex, generating a transformation based on the first set of ECG data, gathering a second set of ECG data from the patient for the base leads for an interval corresponding to at least one ECG complex, and applying the transformation to the second set of ECG data to effect the synthesis of the data for the given lead.

DETAILED DESCRIPTION OF THE INVENTION

In a preferred embodiment of the present invention, a lead is synthesized based on a patient-specific transformation of data acquired on three base leads. The first phase of the present invention involves the generation of the transformation data. The transformation data is generated based on data from the three base leads and data from the lead to be synthesized. In essence, the first phase is a learning process in which a system in accordance with the present invention "learns" the relationship between the base leads and the lead to be synthesized for a specific patient. Once this relationship is "learned," then transformation data for the patient is generated. In the second phase, the present invention inputs data from the three base leads from the patient. It then applies the transformation to this data to generate synthesized data for the lead. The synthesized data is used to analyze the electrocardiographic activity.

In a preferred embodiment, the present invention uses standard leads I, II, and $V_2$ as the three base leads. However, other standard leads and non-standard leads will produce acceptable results. In general, the greater the linear independence of the three base leads, the better the synthesis will be. Indeed, orthogonal leads would tend to maximize linear independence of the leads, but orthogonal placement results in an uncomfortable placement of electrodes.

In a preferred embodiment, the present invention divides the ECG complex into segments. The present invention generates transformation data for each segment. When synthesizing the lead data, the present invention determines in which segment each data point is in and applies the appropriate segment transformation to the base leads.

Figure 1:
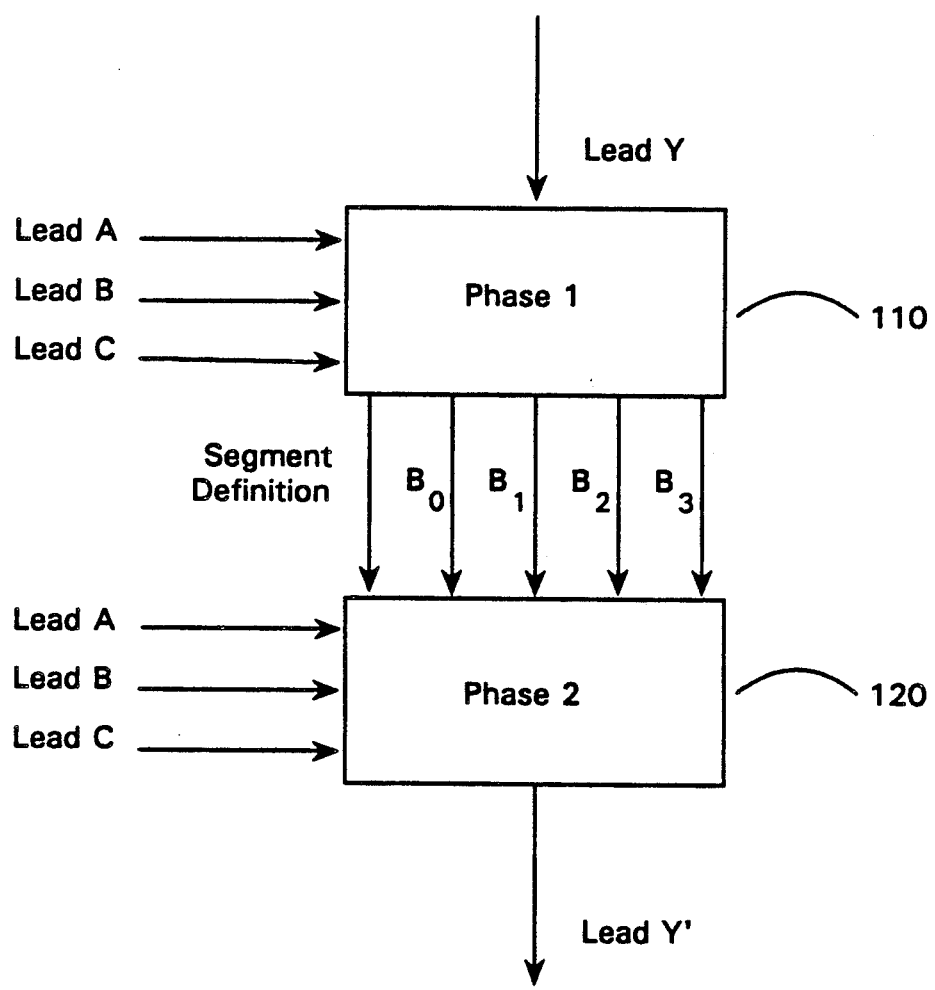
FIG. 1 is a block diagram showing Phase 1 and Phase 2 of a preferred embodiment of the present invention.

FIG. 1 is a block diagram showing Phase 1 and Phase 2 of a preferred embodiment of the synthesis system. In Phase 1 (110) the system generates the segment definitions and the coefficients ($B_0$, $B_1$, $B_2$, and $B_3$) for a linear transformation. The inputs to Phase 1 are the digitized data generated from the three base leads (Lead A, Lead B, and Lead C) and the data from the lead to be synthesized (Lead Y). Phase 1 transfers the segment definitions and the coefficients to Phase 2 (120). Phase 2 generates synthesized data for Lead Y. The output of Phase 2 is Lead Y'. As Phase 2 receives data from the base leads, it generates the data for Lead Y'.

Figure 2:
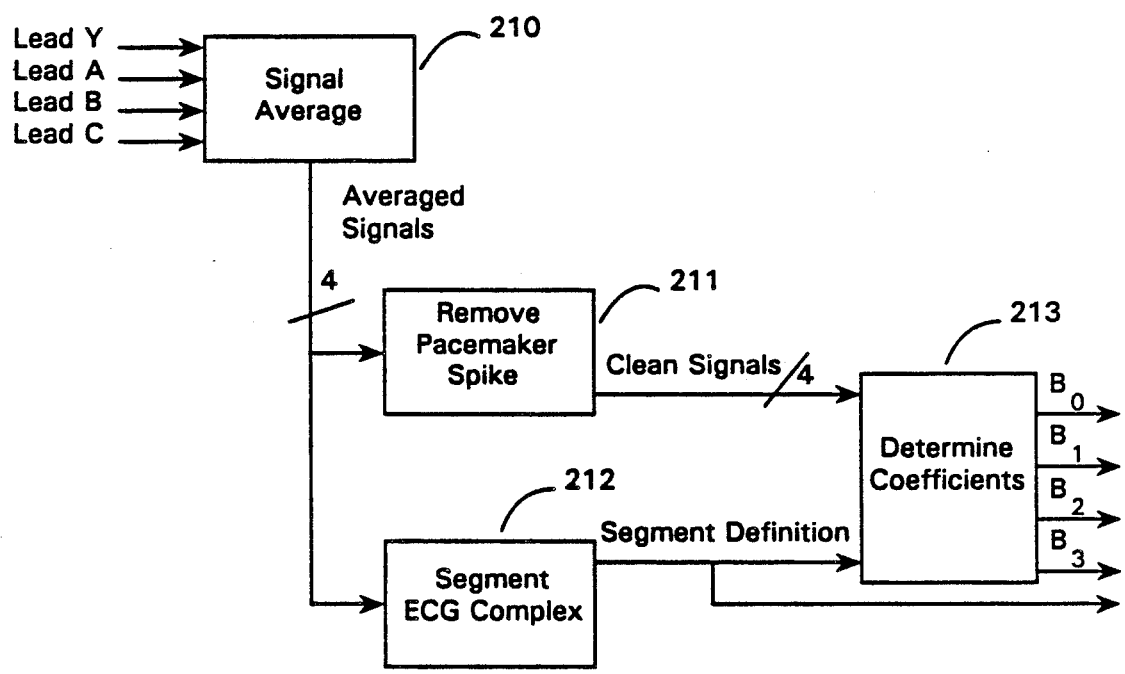
FIG. 2 is a block diagram showing the components of Phase 1 in a preferred embodiment.

FIG. 2 is a block diagram showing the components of Phase 1 in a preferred embodiment. The components illustrated are signal average (210), remove pacemaker spike (211), segment ECG complex (212), and determine coefficients (213). In the signal average component, the system generates an average ECG complex for each of the input leads. In signal analysis, the use of an average signal tends to minimize the effect of noise on the signal. In a preferred embodiment, ten R-R cycles are input for each lead. Alternatively, the system need only consider the ECG complex itself and not the entire R-R cycle. These averaged signals are input to remove pacemaker spike component and segment ECG complex component. In an alternate embodiment, other signal analysis techniques may be used, such as, using the median point of each of the ten cycles as a substitute for the average value. In the remove pacemaker spike component, the system determines if there is a pacemaker spike present in the averaged signals. The techniques for determining whether a pacemaker spike is present are well-known, such as detecting a high-frequency waveform corresponding to a ventricular or atrial spike. The outputs of the remove pacemaker spike component are the averaged signals with any spike removed.

Figure 3:
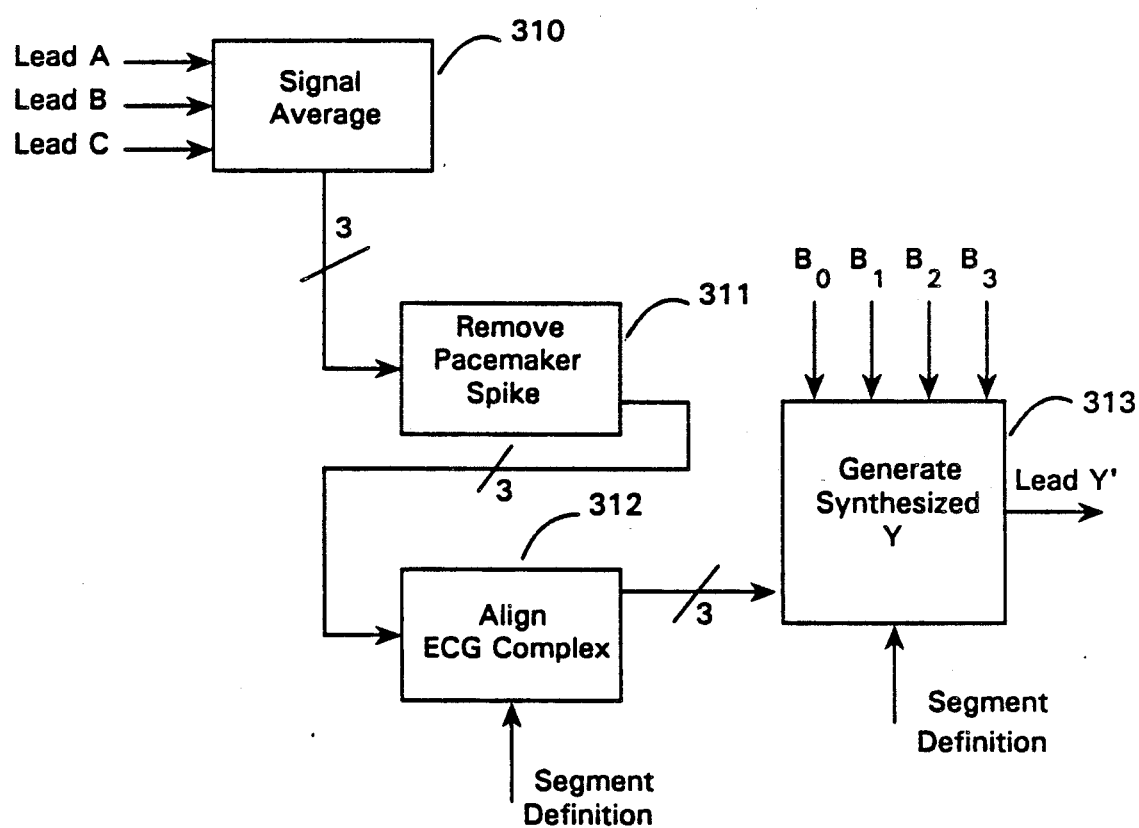
FIG. 3 is a block diagram showing the components of Phase 2 in a preferred embodiment.
Figure 4:
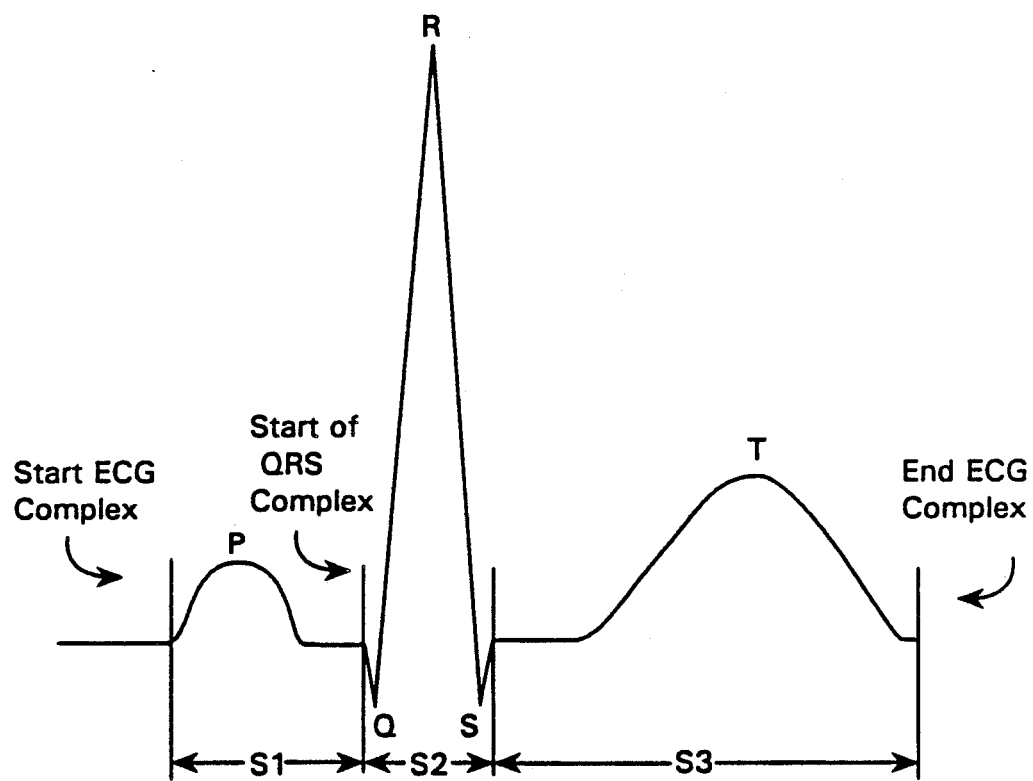
FIG. 4 shows the ECG complex divided into three segments.
Figure 5:
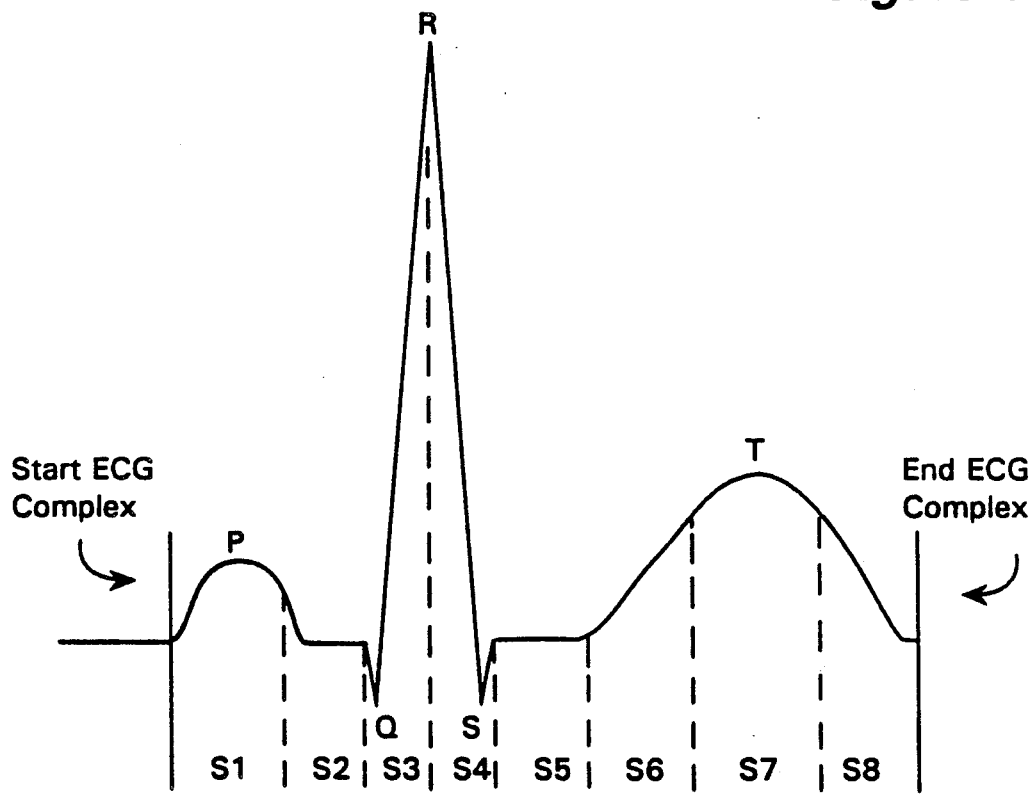
FIG. 5 shows the ECG complex divided into eight segments.
Figure 6:
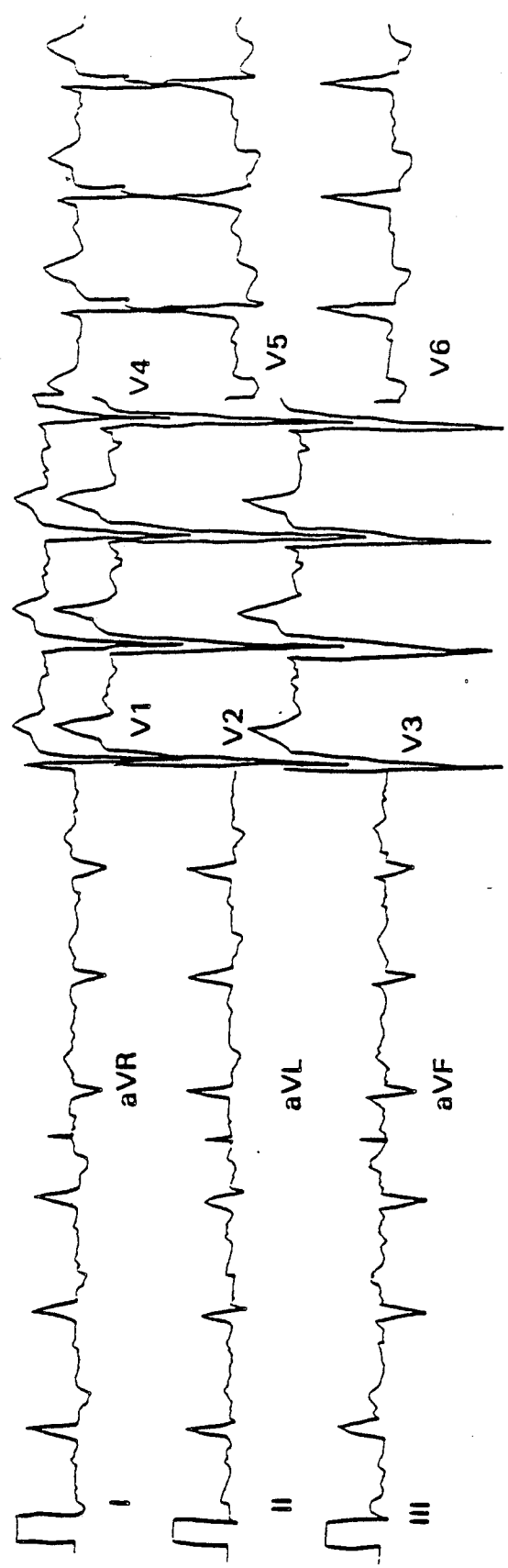
FIG. 6 shows a sample twelve lead ECG.
Figure 7:
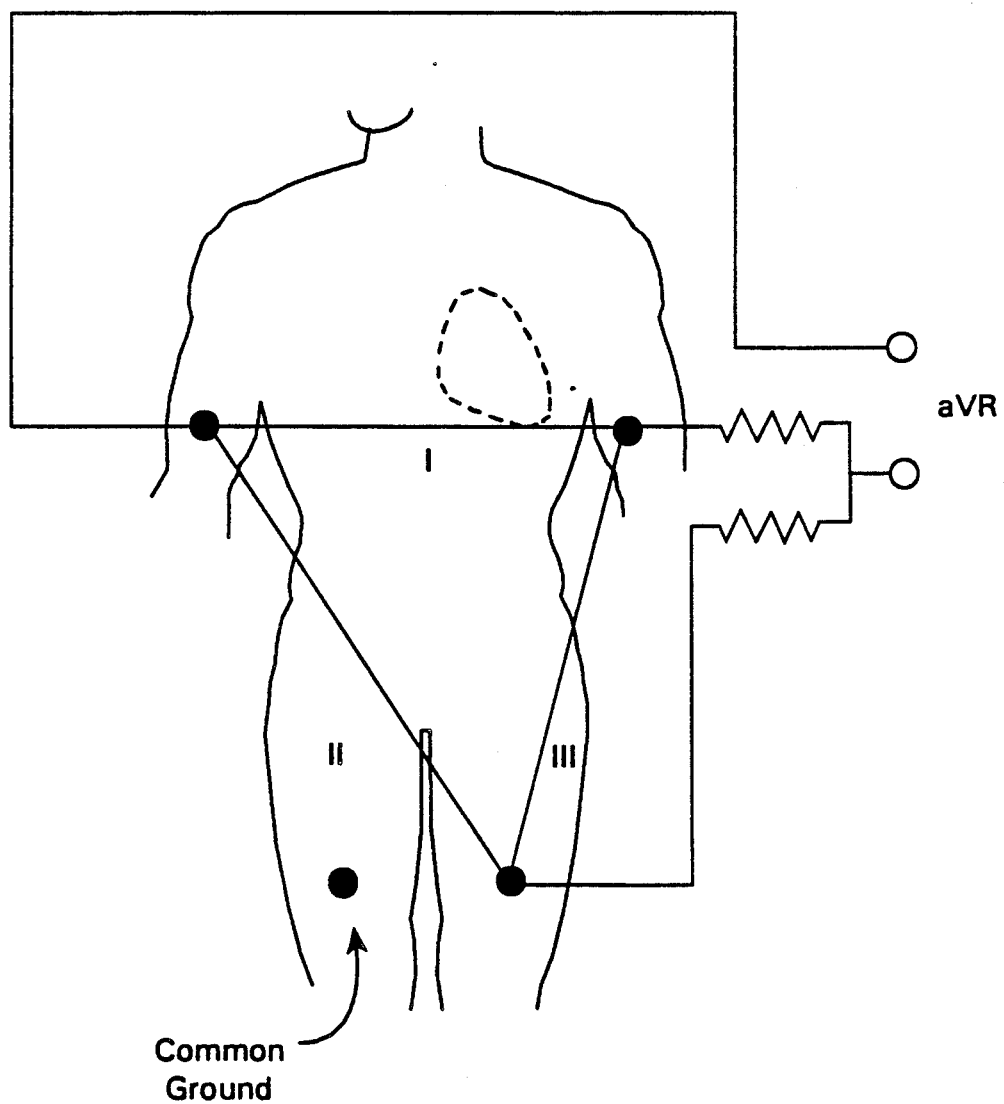
FIG. 7 shows the placement of the electrodes used to generate the six limb leads.
Figure 8:
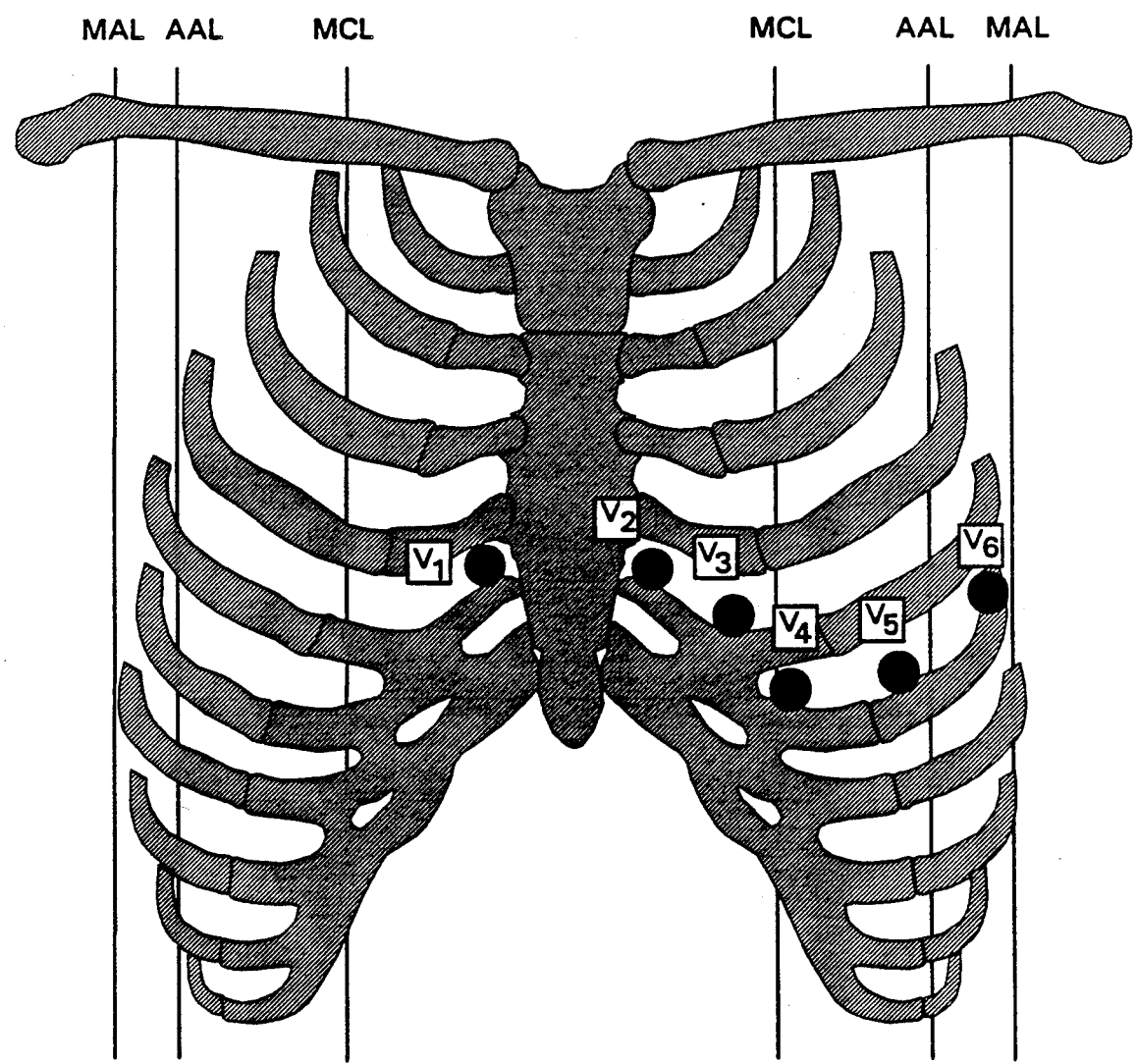
FIG. 8 shows the placement of the electrodes used to generate the six chest leads.

In use segment ECG complex component (212), the system generates a segmentation of the ECG complex. In a preferred embodiment, the segment ECG complex component divides the ECG complex into three segments delimited by [1] the beginning of the ECG complex, [2] the beginning of the QRS complex, [3] the end of the QRS complex, and [4] the end of the ECG complex. FIG. 3 illustrates the three segments of the ECG complex. In an alternate preferred embodiment, the segment ECG complex component further subdivides the segments of the ECG complex. As illustrated in FIG. 5, the ECG complex is divided into eight segments. The eight segments are divided by [1] the start of the ECG complex, [2] the midpoint between the start of the ECG complex and the beginning of the QRS complex, [3] the beginning of the QRS complex, [4] the midpoint between the beginning of the QRS complex and the end of the QRS complex, [5] the end of the QRS complex, [6] the quarter point between the end of the QRS complex and the end of the ECG complex, [7] the midpoint between the end of the QRS complex and the end of the ECG complex, [8] the three-quarter point between the end of the QRS complex and the end of the ECG complex, and [9] the end of the ECG complex. Other segmentation techniques, such as using fixed time intervals from the start of the ECG complex, will produce acceptable results. The segment definitions are inputs that determine coefficients component. The determine coefficients component generates transformation coefficients to be used in the synthesize of Lead Y. Other segmentation techniques, such as using time intervals generally corresponding to the start of the ECG complex, will produce acceptable results. In a preferred embodiment, the coefficients for a linear solution are generated using least squares analysis. Although the solution to the linear equation produces acceptable results, polynomial solutions also produce acceptable results. In addition, other curve-fitting solution may produce acceptable results. In an preferred embodiment, the outputs of determine coefficients (213) are the linear regression coefficients, $B_0$, $B_1$, $B_2$, and $B_3$.

FIG. 3 is a block diagram showing the components of Phase 2 in a preferred embodiment. The components illustrated are signal average (310), remove pacemaker spike (311), align ECG complex (312), and the generate synthesized Y (313). In the signal average component, the system generates an averaged signal for each of Leads A, B, and C. In a preferred embodiment, the system generates a running average of the last ten ECG complexes received. Various signal analysis techniques as described above for the signal average component (210) can be used. The signal average data is used as input to the remove pacemaker spike component and the align ECG complex component. The remove pacemaker spike component performs essentially the same function as described above for the remove pacemaker spike (211). The ECG complex component ensures that the ECG complex is aligned with the data processed in Phase 1. This alignment ensures that the coefficients will be applied to the proper segments. In the generate synthesized Y component, the system generates a synthesized Lead Y (Lead Y') based on the aligned signals for Leads A, B, and C, the coefficients, and the segment definition. In a preferred embodiment, a synthesized point of data is generated by the following equation:

$$Y_i' = B_0 + B_1 {}^*A_i + B_2 {}^*B_i + B_3 {}^*C_i$$

where i indicates the ith data point in the ECG complex, $B_j$ indicates the coefficients for the segment that contains the ith data point, and $A_i$, $B_i$, and $C_i$ indicate the signal averaged data for the ith data point for leads A, B, and C.

Figure 9:
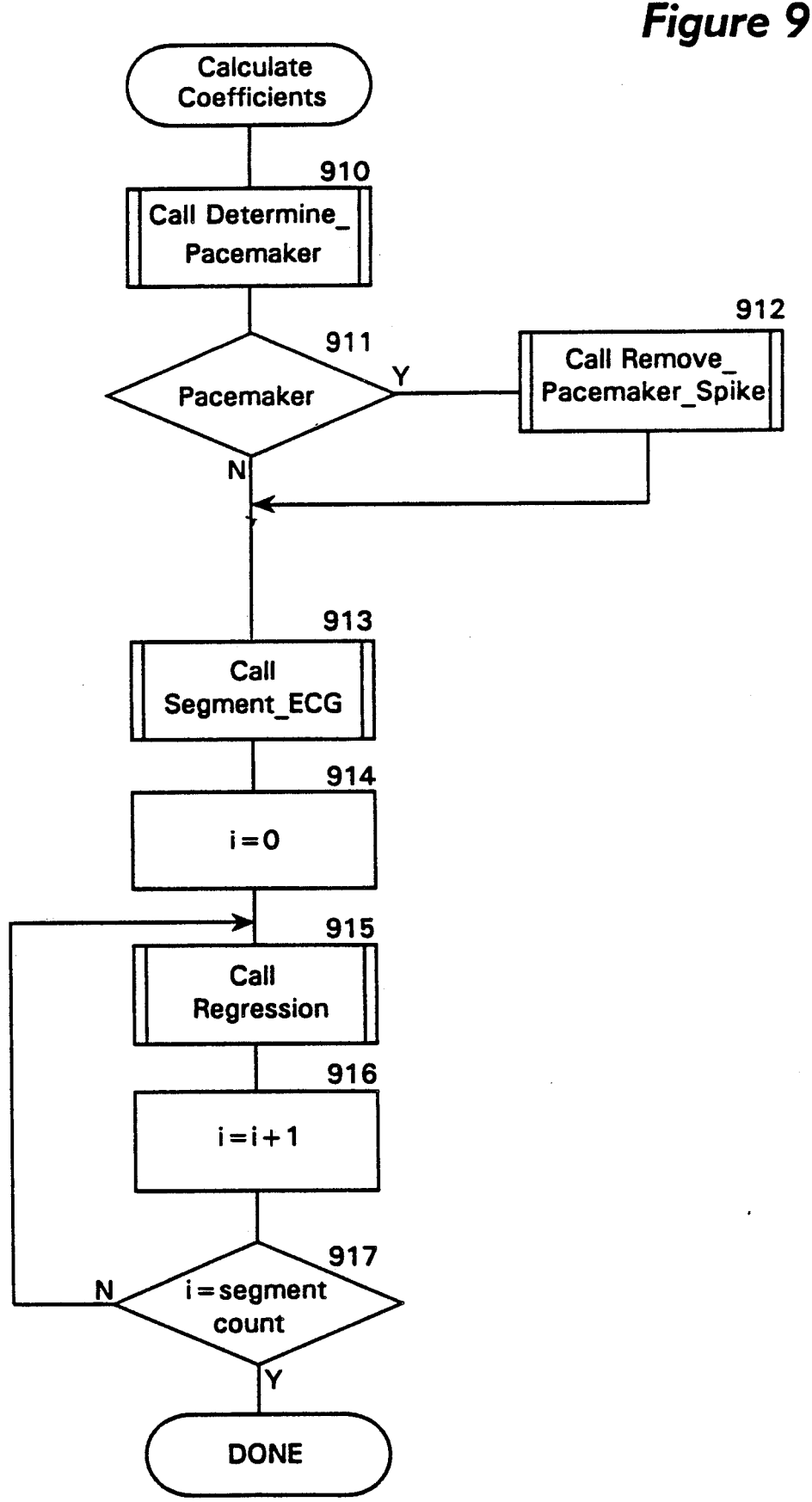
FIG. 9 is a flow diagram of calculate coefficients routine.

In a preferred embodiment, the present invention is implemented in a computer based system. However, the present invention can be implemented using discrete logic in whole or in part. FIG. 9 is a flow diagram of a computer routine that generates the transformation coefficients. The input to this routine is an array containing the digitized data for leads I, II, and $V_2$ and for the lead to be synthesized. In a preferred embodiment, the array contains 300 entries for each lead. The data is sampled at a rate of 250 Hz. In a preferred embodiment, the data is gathered over ten R-R cycle periods. For each lead, the ECG's are aligned and a signal analysis technique is employed to minimize noise on the signal. In a preferred embodiment, the median point for each of the ten R-R cycles is used as a substitute for the average. Alternatively, the average value of the ten data points can be used. The output of this routine is the coefficients for the linear transformation. The signal averaged data is stored in array ecg[300][4], which contains data for the base leads, and array y [300], which contains data for the lead to be synthesized (see blocks 10A12 and 10H13). Columns 1, 2, and 3 of array ecg contain the base lead data and column 0 contains all 1's and is used to calculate a dc-offset (y-intercept of the line defined by the array and each of the two leads) for each segment.

In block 910, the system invokes subroutine Determine_Pacemaker, which analyzes the leads to determine whether the data was collected from a patient with a pacemaker. Subroutine Determine_Pacemaker returns a flag that indicates whether a pacemaker is present and it returns an index in array ecg specifying the highest point of the pacemaker spike. In block 911, if the pacemaker flag is true, then the system continues at block 912 to call subroutine Remove_Pacemaker_Spike, else the system continues at block 913. The techniques for detecting and removing pacemaker spikes are well-known.

In block 913, the system calls subroutine Segment_ECG. Subroutine Segment_ECG analyzes the data in array ecg to determine the segments, and returns the start and stop indices into array ecg, which define each segment boundary, and the number of segments in variable segment_count. The start and stop indices are returned in an array. The techniques for detecting the boundaries for the segments as described above are well known. In blocks 914 through 917, the system executes a loop that calculates the coefficients for each segment. When the loop completes, the coefficients are stored in array B. Array B is an array with four columns (one for each base lead and one for the dc-offset) and a number of rows equal to the number of segments. In block 914, the system initializes the loop control variable i to 0. In block 915, the system calls subroutine Regression, which determines the coefficients for the specified segment and stores the coefficients in array B. FIGS. 10A through 10I comprise a flow diagram for the regression subroutine. In block 916, the system increments the loop variable i. In block 917, if the loop variable i equals segment_count, then coefficients for all the segments have been generated and the routine is done, else the system continues at block 915 to generate coefficients for the next segment.

FIGS. 10A through 10I comprise a flow diagram of subroutine Regression. The input parameters to subroutine Regression are array ecg (which contains the data for leads I, II, and $V_2$ and is in column 0), array y (which contains the data for the lead to be synthesized), and variables start and stop (which are indices into the data arrays delimiting the segment boundaries). The output of subroutine Regression is array B, which contains the coefficients for the linear transformation for the lead to be synthesized. The coefficients for the linear transformation are defined by the following equation:

$$B = (ecg^t {}^* ecg)^{-1} {}^* (ecg^t {}^* y)$$

where $ecg^t$ is the transpose of matrix ecg and $^{-1}$ indicates matrix inversion.

Figure 10A:
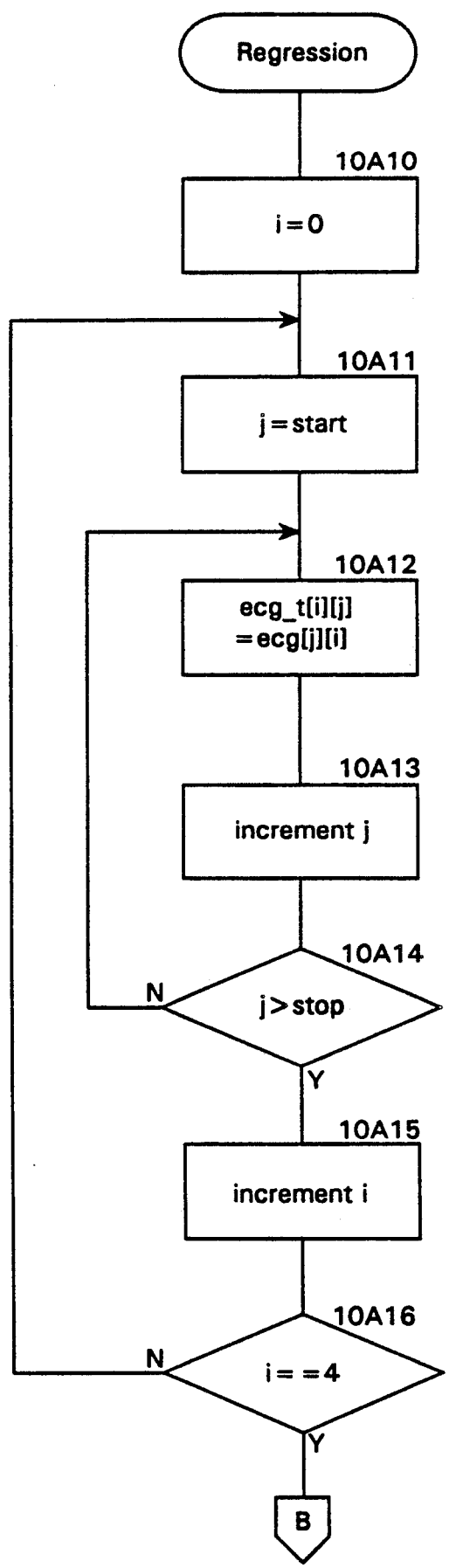
FIGS. 10A through 10I comprise a flow diagram for the regression routine.

In FIG. 10A, the system calculates the transpose of ecg between start and stop and stores the transpose in array ecg_t. Array ecg_t is a 4-by-300 array. In block 10A10, the system initializes loop variable i to 0. In block 10A11, the system initializes inner loop variable j to equal parameter start, which is the index to the start of the segment in ecg. In block 10A12, the system set ecg_t[i][j] equal to ecg[j][i]. In block 10A13, the system increments loop variable j. In block 10A14, if loop variable j is greater than parameter stop (which indicates the end of the segment), then the system continues at block 10A15, else the system loops to block 10A12 to continue with the transposition of the matrix. In block 10A15, the system increments loop variable i. In block 10A16, if loop variable i equals 4, then the matrix transposition is complete and the system continues at block 10B10 of FIG. 10B, else the system loops to block 10A11 to continue with the transposition of the matrix.

Figure 10B:
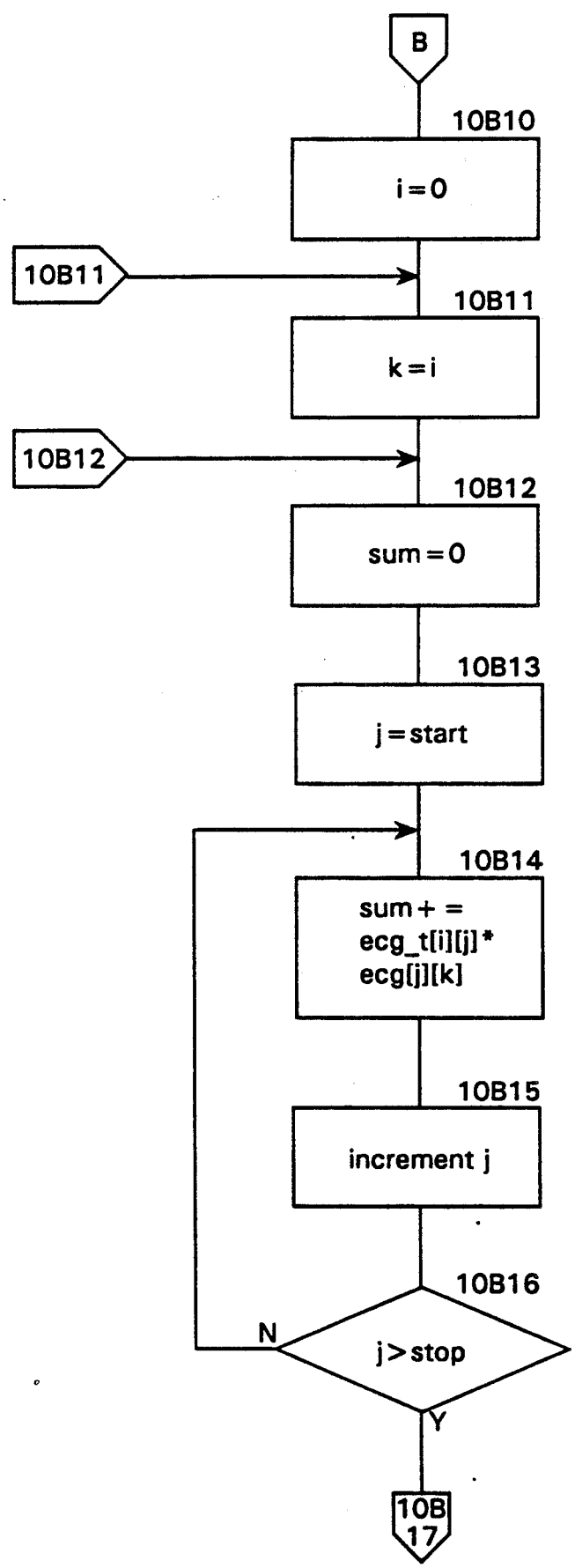
Figure 10B:
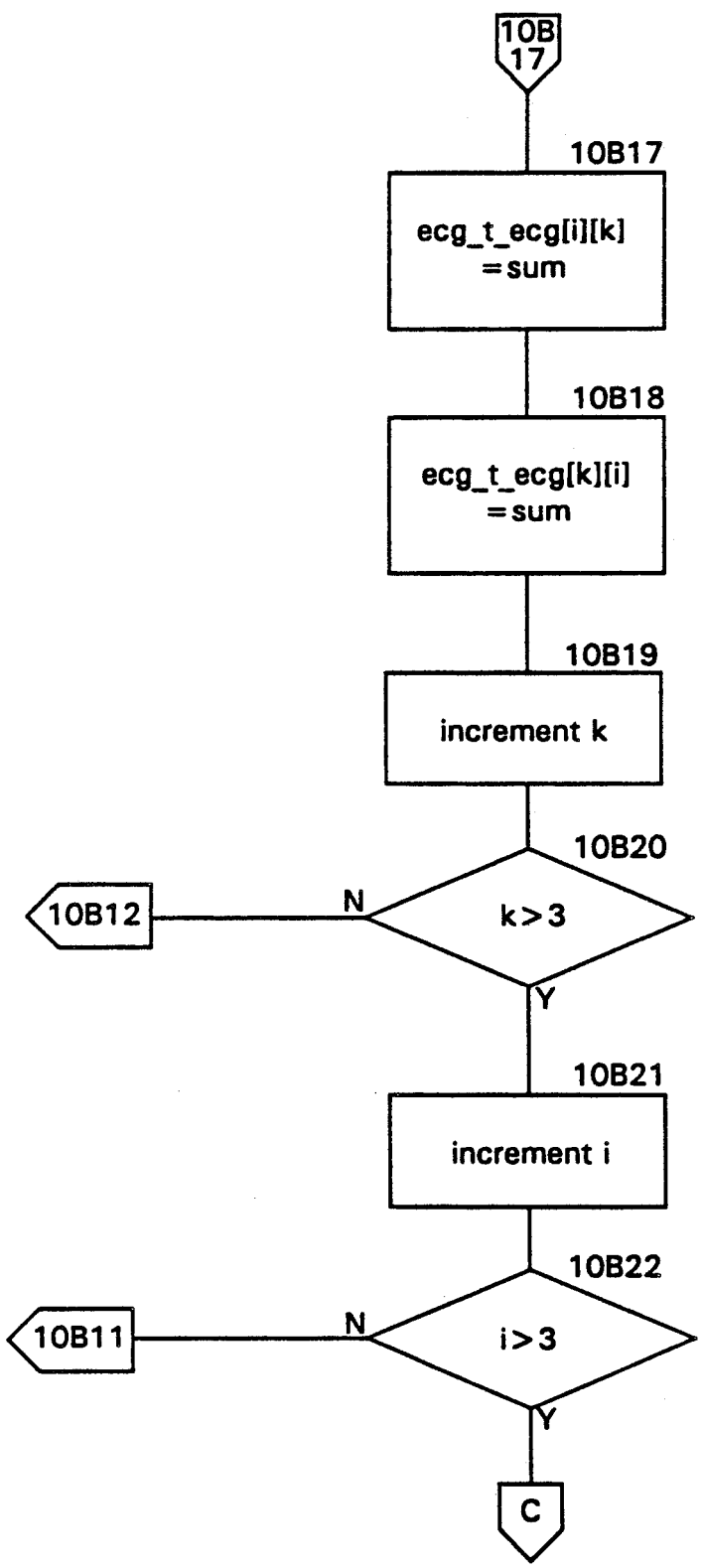

In FIG. 10B, the system multiplies ecg_t times ecg and stores the result in array ecg_t_ecg, which is a 4-by-4 array. In block 10B10, the system initializes loop variable i to 0. Loop variable i controls the looping through each of the four rows in ecg_t. In block 10B11, the system sets loop variable k equal to variable i. Loop variable k controls the looping through each of the four columns of ecg. Loop variable k is initialized to i rather than 0 because the product of a matrix and its transpose is a matrix that is symmetric about the diagonal. In block 10B12, the system sets variable sum equal to 0. In block 10B13, the system sets loop variable j equal to parameter start. Loop variable j controls the looping through the segment data. In block 10B14, the system increments variable sum by the product of ecg_t[i][j] times ecg[j][k]. In block 10B15, the system increments loop variable j. In block 10B16, if loop variable j is greater than parameter stop, then all the data for the segment has been processed and the system continues at block 10B17, else the system loops to block 10B14. In blocks 10B17 and 10B18, the system sets the symmetrical entries in the resulting matrix. In block 10B17, the system set ecg_t_ecg[i][k] equal to variable sum. In block 10B18, the system sets ecg_t_ecg[k][i] equal to variable sum. In block 10B19, the system increments loop variable k. In block 10B20, if loop variable k is greater than 3, then each of columns of array ecg has been processed and the system continues at block 10B21, else the system loops to block 10B12. In block 10B21, the system increments loop variable i. In block 10B22, if loop variable i is greater than 3, then all the rows of array ecg_t have been processed and the system continues at block 10C10 of FIG. 10C, else the system loops to block 10B11.

Figure 10C:
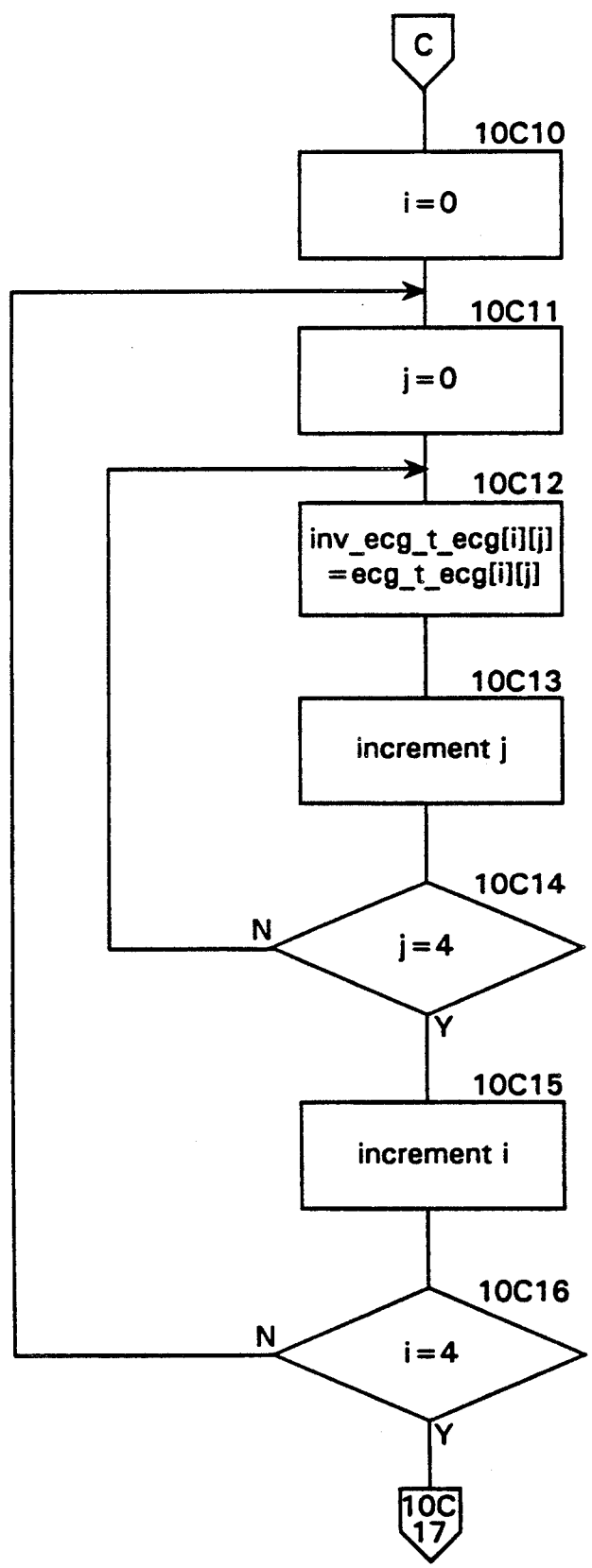
Figure 10C:
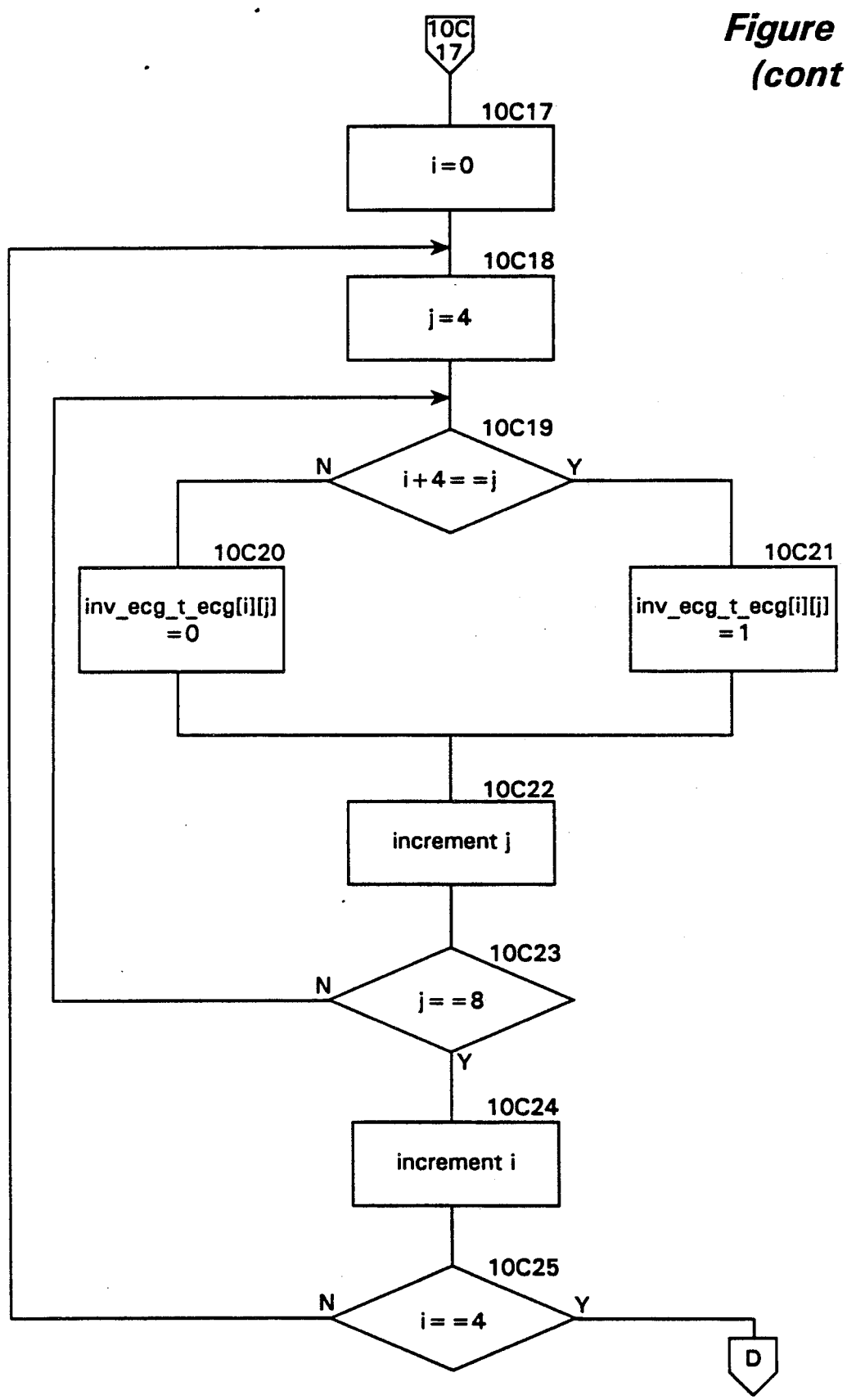

FIGS. 10C through 10F are a flow diagram for the inversion of matrix ecg_t_ecg. In a preferred embodiment, the system uses the Gauss-Jordan inversion technique. Array inv_ecg_t_ecg is an 4-by-8 array. This matrix is used for calculating the inverted matrix and for storing the inverted matrix in columns 0 through 3. In FIG. 10C, the system initializes matrix inv_ecg_t_ecg for the matrix inversion. Columns 0 through 3 are initialized to contain array ecg_t_ecg and columns 4 through 7 are initialized to contain the identity matrix, that is, to contain 1's in the diagonal and 0's elsewhere. In blocks 10C10 through 10C16, the system copies array ecg_t_ecg into columns 0 through 3 of array inv_ecg_t_ecg. In block 10C10, the system initializes loop variable i to 0. In block 10C11, the system initializes loop variable j to 0. In block 10C12, the system sets inv_ecg_t_ecg[i][j] to ecg_t_ecg[i][j]. In block 10C13, the system increments loop variable j. In block 10C14, if loop variable j equals 4, then all the columns for the row specified by variable i have been processed and the system continues at the next row in block 10C15, else the system loops to block 10C12. In block 10C15, the system increments loop variable i. In block 10C16, if loop variable i equals 4, then all the rows have been processed and the system continues at block 10C17, else the system loops to process the next row at block 10C11.

In blocks 10C17 through 10C25, the system sets columns 4 through 7 of inv_ecg_t_ecg equal to the identity matrix. In block 10C17, the system initializes loop variable i to 0. In block 10C18, the system initializes loop variable j to 4. In block 10C19, if loop variable i plus 4 equals loop variable j, then the loop variables index the diagonal of the matrix and the system continues at block 10C21, else the system continues at block 10C20. In block 10C20, the system sets the non-diagonal element inv_ecg_t_ecg[i][j] equal to 0. In block 10C21, the system sets the diagonal element inv_ecg_t_ecg[i][j] equal to 1. In block 10C22, the system increments loop variable j. In block 10C23, if loop variable j equals 8, then all the columns for the specified row have been set and the system processes the next row at block 10C24, else the system loops to block 10C19. In block 10C24, the system increments loop variable i. In block 10C25, if loop variable i equals 4, then all the rows have been processed and the system continues at block 10D10 in FIG. 10D, else the system loops to block 10C18.

Figure 10D:
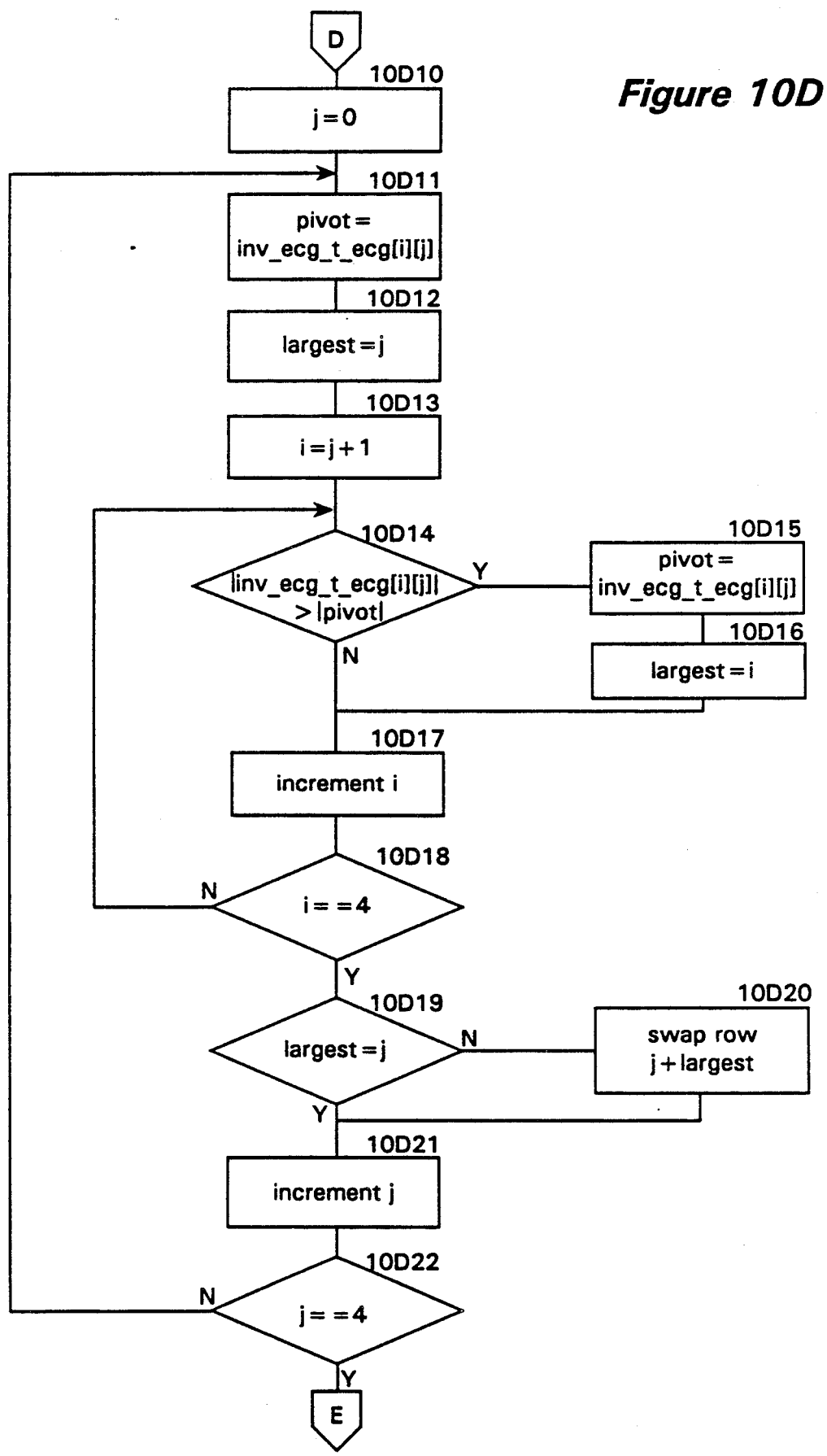

FIG. 10D is a flow diagram of a portion of the matrix inversion employing partial pivoting that ensures that for each of columns 0 through 3 the diagonal value is greater than the values below the diagonal in array inv_ecg_t_ecg. The system swaps the rows of the array to ensure this. In block 10D10, the system initializes loop variable j to 0. In block 10D11, the system sets variable pivot equal to inv_ecg_t_ecg[j][j]. In block 10D12, the system sets variable largest equal to variable j. In block 10D13, the system initializes variable i to equal variable j plus 1. In block 10D14, if the absolute value of inv_ecg_t_ecg[i][j] is greater than the absolute value of variable pivot, then the element indexed by variables i and j is greater than the other elements above it in the column but at or below the diagonal and the system continues at block 10D15, else the system continues at 10D17. In blocks 10D15 and 10D16, the system resets variables pivot and largest. In block 10D15, the system sets variable pivot equal to inv_ecg_t_ecg[i][j]. In block 10D16, the system sets variable largest equal to variable i. In block 10D17, the system increments variable i. In block 10D18, if loop variable i equals 4, then all the rows in the specified column have been processed and the system continues at block 10D19, else the system loops to block 10D14. In block 10D19, if variable largest equals variable j, then the diagonal contains the largest element and the system continues at block 10D21, else the system continues at block 10D20. In block 10D20, the system swaps the elements in the rows indexed by variables j and largest. In block 10D21, the system increments loop variable j. In block 10D22, if loop variable j equals 4, then columns 0 through 3 have been processed and the system continues at block 10E10 in FIG. 10E, else the system loops to block 10D11.

Figure 10E:
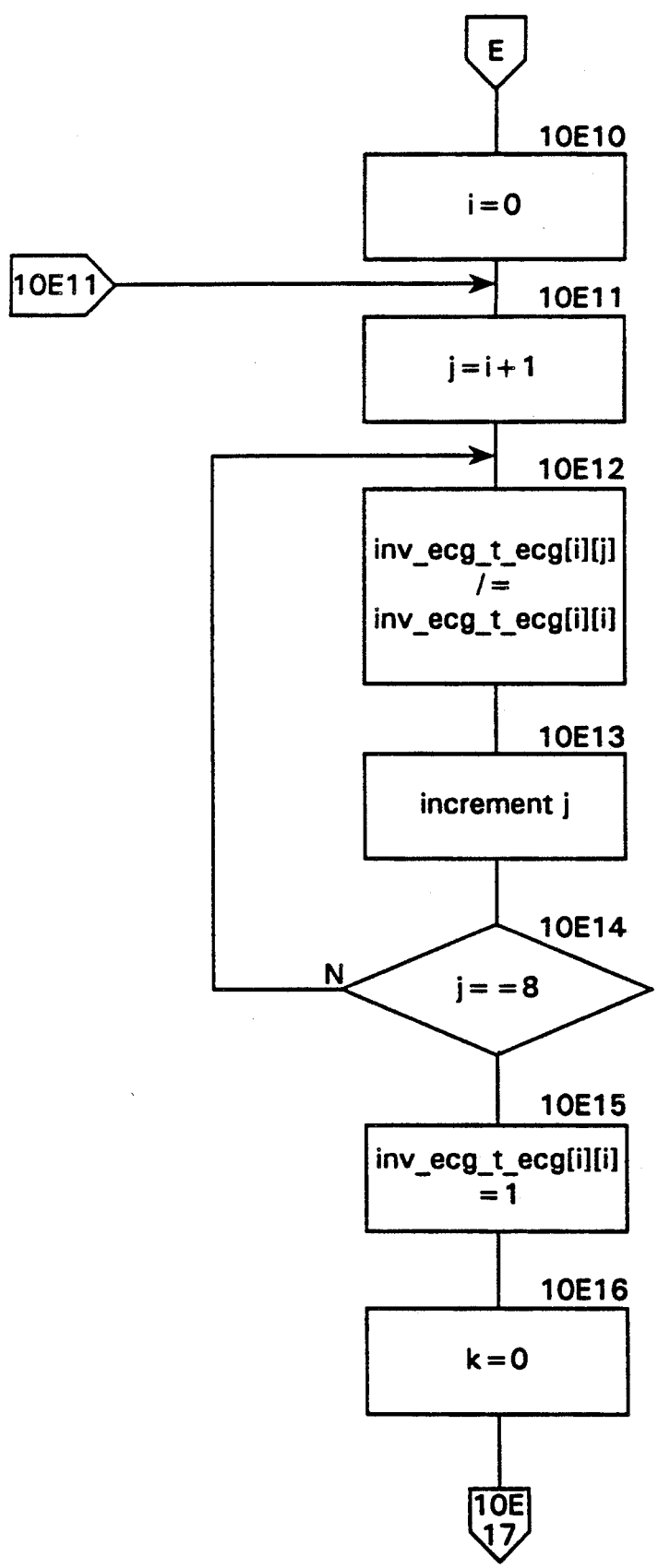
Figure 10E:
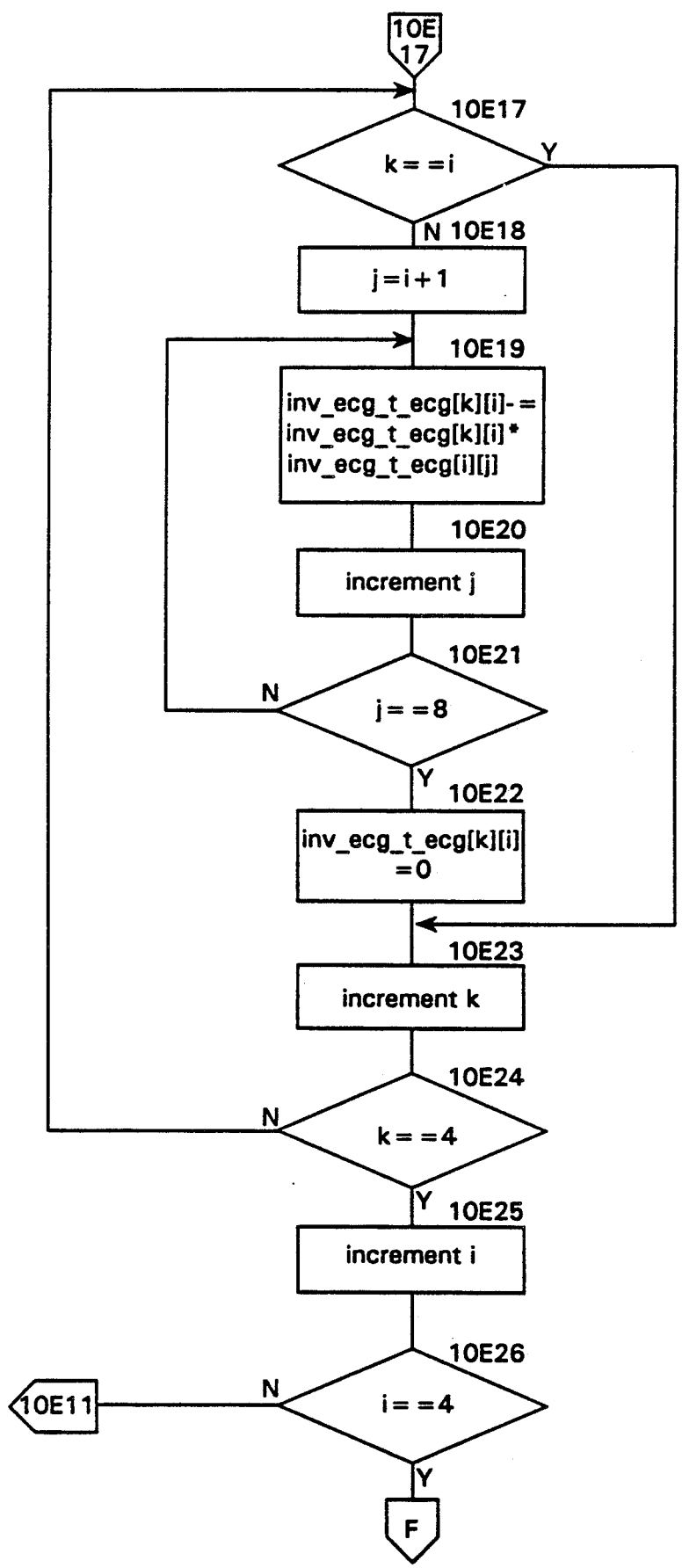

In FIG. 10E, the system generates the inverted matrix in columns 4 through 7 of array inv_ecg_t_ecg. In block 10E10, the system initializes loop variable i to 0, which controls the looping through the rows. In block 10E11, the system initializes loop variable j equal to variable i plus 1. Loop variable j controls looping through row numbers greater than that specified by variable i. In block 10E12, the system divides the element at inv_ecg_t_ecg[i][j] by inv_ecg_t_ecg[i][i]. In block 10E13, the system increments loop variable j. In block 10E14, if loop variable j equals 8, then the dividing of the elements in the specified row is complete and the system continues at block 10E15, else the system loops to block 10E12. In block 10E15, the system sets inv_ecg_t_ecg[i][i] equal to 1. In block 10E16, the system initializes loop variable k to 0, which is an index to the rows. In block 10E17, if variable k equals variable i, then the system continues at block 10E23, else the system continues at block 10E18. In block 10E18, the system initializes variable j equal to variable i plus 1. In block 10E19, the system subtracts inv_ecg_t_ecg[k][i] times inv_ecg_t_ecg[i][j] from inv_ecg_t_ecg[k][j]. In block 10E20, the system increments loop variable j. In block 10E21, if loop variable j equals 8, then the elements in the specified row have been processed and the system continues at block 10E22, else the system loops to block 10E19. In block 10E22, the system sets inv_ecg_t_ecg[k][i] equal to 0. In block 10E23, the system increments loop variable k. In block 10E24, if loop variable k equals 4 then each row has been processed and the system continues at block 10E25, else the system loops to block 10E17. In block 10E25, the system increments variable i. In block 10E26, if loop variable i equals 4, then the matrix inversion is complete and the system continues at block 10F10 of FIG. 10F, else the system loops to 10E11.

Figure 10F:
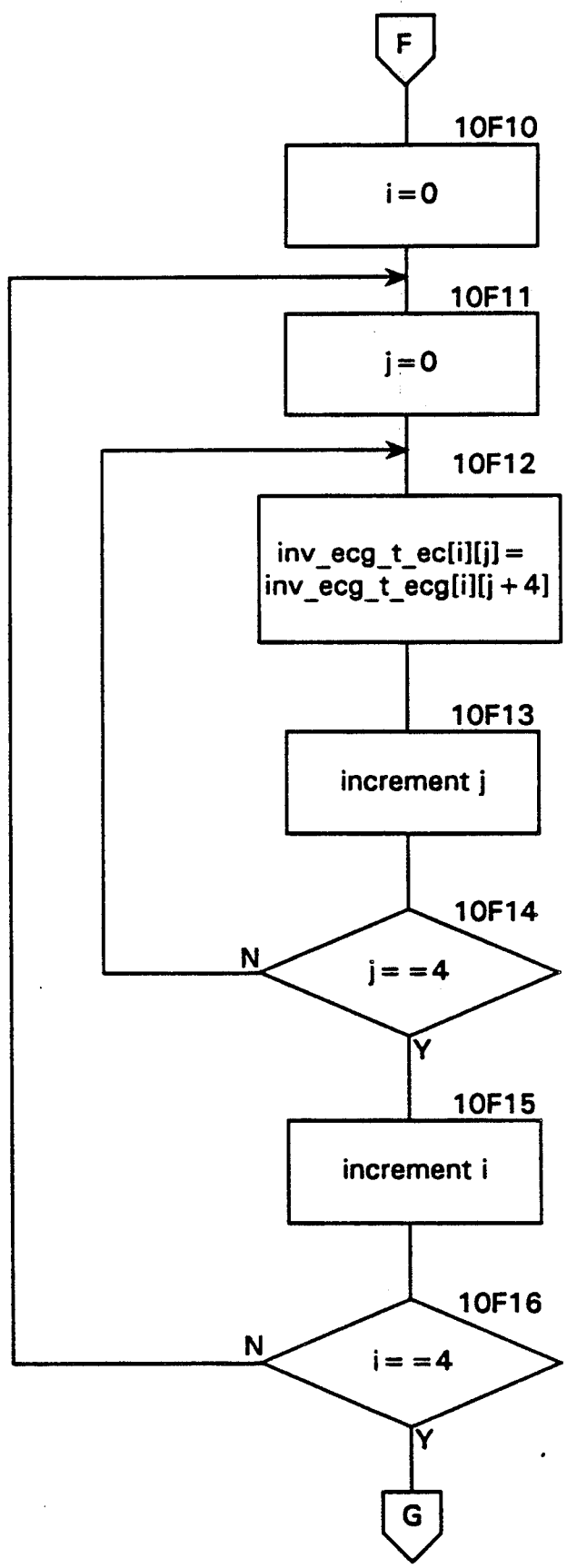

In FIG. 10F, the system moves the inverse matrix from columns 4 through 7 of inv_ecg_t_ecg to columns 0 through 3. In block 10F10, the system initializes loop variable i to 0. In block 10F11, the system initializes loop variable j to 0. In block 10F12, the system sets inv_ecg_t_ecg[i][j] to inv_ecg_t_ecg[i][j+4]. In block 10F13, the system increments loop variable j. In block 10F14, if loop variable j equals 4, then each element in the specified row has been copied and the system continues at block 10F15, else the system loops to block 10F12. In block 10F15, the system increments loop variable i. In block 10F16, if loop variable i equals 4, then all the rows have been moved and the system continues at block 10G10 in FIG. 10G, else the system loops to block 10F11.

Figure 10G:
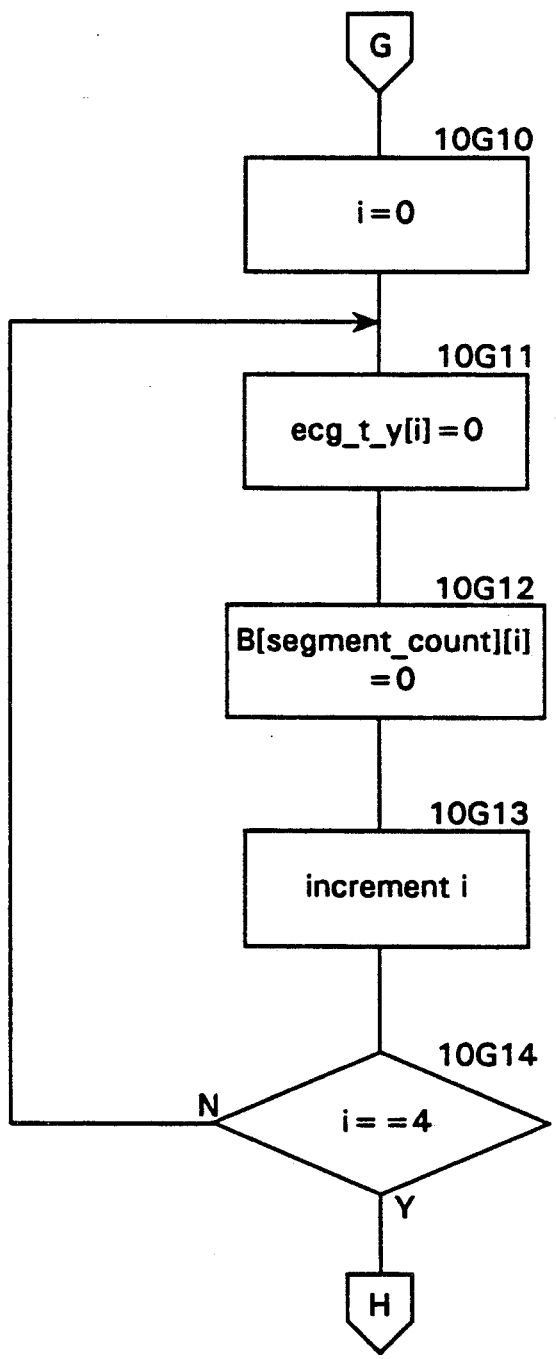

FIG. 10G is flow diagram showing the initialization of arrays ecg_t_y[4], which will contain the product of array ecg_t times array y, and B, which will contain the coefficients. In block 10G10, the system initializes loop variable i to 0. In block 10G11, the system initializes ecg_t_y[i] to 0. In block 10G12, the system initializes B[segment-count][i] to 0, where segment count holds the index for the current segment. In block 10G13, the system increments loop variable i. In block 10G14, if loop variable i equals 4, then each element in the arrays has been initialized and the system continues at block 10H10 in FIG. 10H, else the system loops to block 10G11.

Figure 10H:
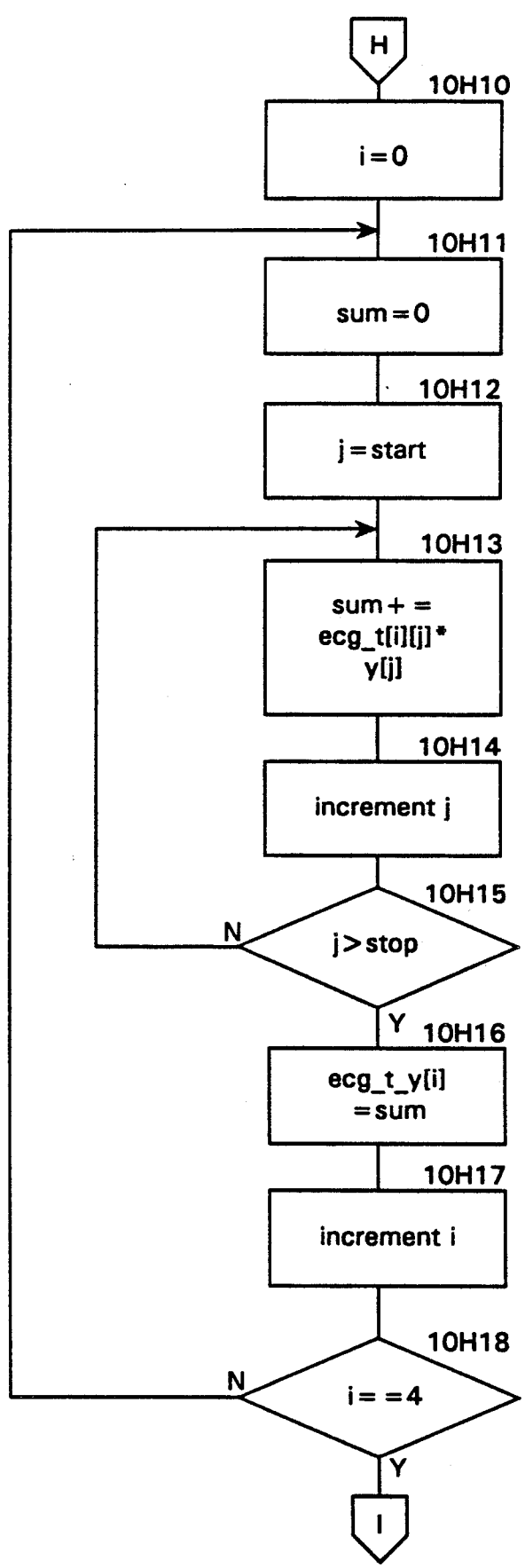

FIG. 10H is a flow diagram showing the matrix multiplication of ecg_t times y. The result is stored in array ecg_t_y, which is a 4-element array. In block 10H10, the system initializes loop variable i to 0. In block 10H11, the system initializes variable sum to 0. In block 10H12, the system initializes loop variable j by setting it equal to variable start. In block 10H13, the system adds ecg_t[i][j] times y[j] to the variable sum. In block 10H14, the system increments loop variable j. In block 10H15, if loop variable j is greater than variable stop, then the system continues at block 10H16, else the system loops to block 10H13. In block 10H16, the system sets ecg_t_y[i] equal to variable sum. In block 10H17, the system increments variable i. In block 10H18, if loop variable i equals 4, then the system continues at block 10I10 of FIG. 10I, else the system loops to block 10H11.

Figure 10I:
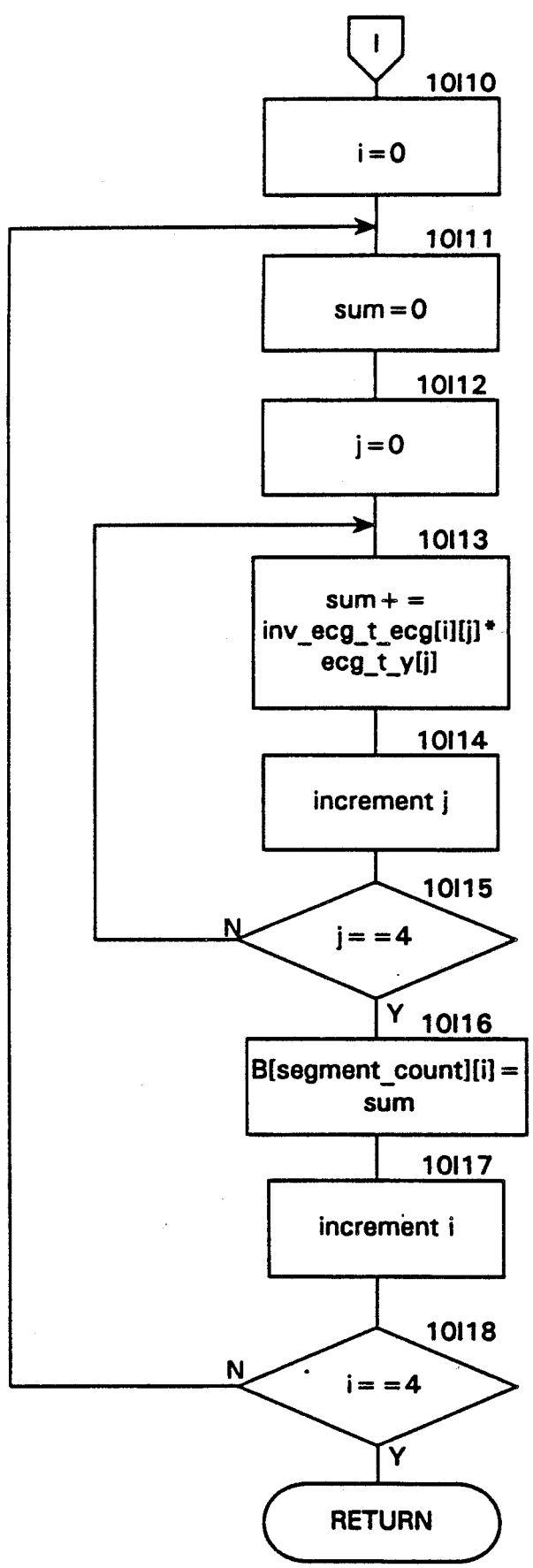

FIG. 10I is a flow diagram showing the matrix multiplication of inv_ecg_t_ecg times ecg_t_y. In block 10I10, the system initializes loop variable i to 0. In block 10I11, the system initializes variable sum to 0. In block 10I12, the system initializes loop variable j to 0. In block 10I13, the system adds inv_ecg_t_ecg[i][j] times ecg_t_y[j] to variable sum. In block 10I14, the system increments loop variable i. In block 10I15, if loop variable j equals 4, then the system continues at block 10I16, else the system loops to 10I13. In block 10I16, the system sets B[segment-count][i] equal to variable sum. In block 10I17, the system increments loop variable i. In block 10I18, if loop variable i equals 4, then calculation of the coefficients is complete and subroutine Regression returns, else the system loops to block 10I11.

Figure 11:
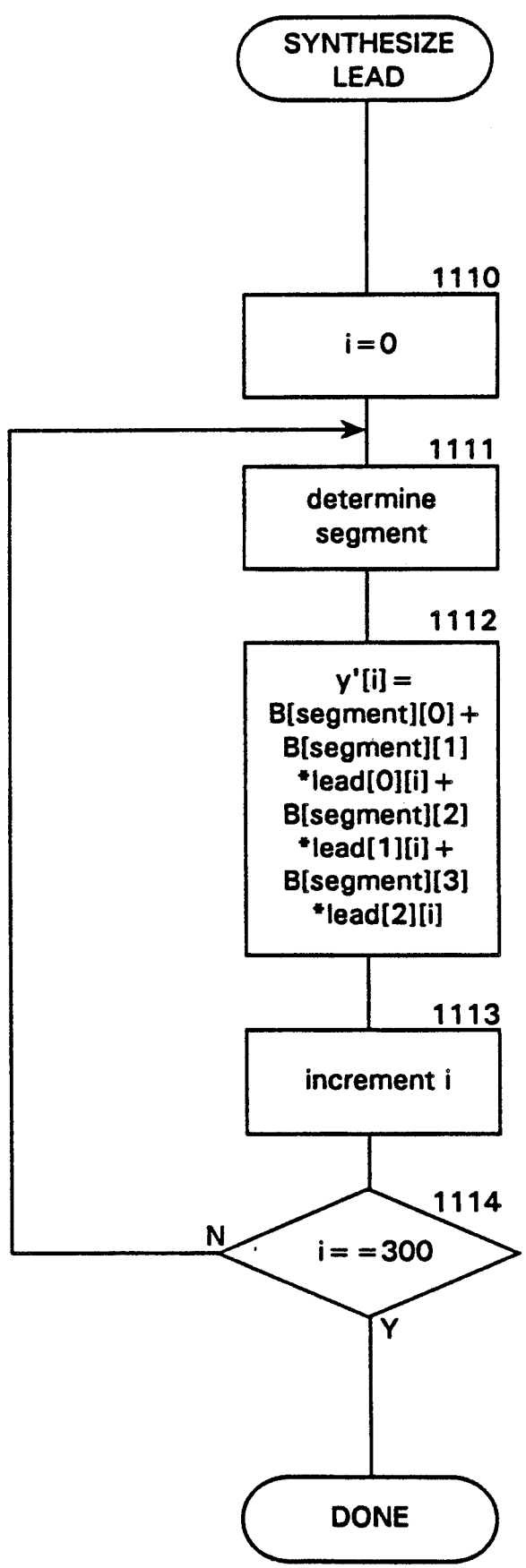
FIG. 11 is a flow diagram of the synthesized lead routine.

FIG. 11 is a flow diagram of routine Synthesize_Lead. The input to routine Synthesize_Lead is the array of coefficients B, the segment boundaries, and the signal averaged data from the three base leads which is stored in array lead[3][300]. The routine generates the synthesized data for one ECG complex and stores the result in array y, which is a 300 element array. In block 1110, the system initializes loop variable i to 0. In block 1111, the system determines in which segment the element index by variable i is in. Variable segment is set to that segment. Variable segment is used as an index into array B to select the coefficients for the appropriate segment. In block 1112, the system sets y[i] equal to B[segment][0] plus B[segment][1] times lead[0][i] plus B[segment][2] times lead[1][i] plus B[segment][3] times lead[2][i]. The addition of B[segment][0], which corresponds to dc-offset, aligns the segments. Without adding in the dc-offset, the synthesized data has unacceptable inter-segment gaps. In an alternate embodiment, the inter-segment gaps are effectively removed by a multivariate regression to mean 0. In block 1113, the system increments loop variable i. In block 1114, if loop variable i equals 300, then the generation of the synthesized lead is complete; else the system loops to block 1111.

Although the present invention has been described in terms of a preferred embodiment, it is not intended that the invention be limited to these embodiments. Modifications within the spirit of the invention will be apparent to those skilled in the art. For example, generation of the coefficients using polynomial equations will produce acceptable results. Also, it will be apparent to one skilled in the art that the use of segmentation can be applied to population-based synthesis to produce improved results. It will also be apparent to one skilled in the art that the segmentation techniques of the present invention can be applied to data gathered from both orthogonal leads and non-orthogonal leads. It will also be apparent to one skilled in the art that non-standard leads can be synthesized by the present invention. It will also be apparent to one skilled in the art that determination of the coefficients can be made after a period of collecting data for the base leads. Thus, in the case of a medical emergency, the base lead data can be collected, then the coefficients determined and applied retrospectively, to analyze the ECG. It will also be apparent to one skilled in the art that the base leads data can be collected and the synthesis can be performed in a batch mode rather than in real-time. It will also be apparent to one skilled in the art that the 12 lead ECG can be synthesized from only three leads. Initially, data for leads I, II, $V_1$, $V_2$, $V_3$, $V_4$, $V_6$ are collected. Then the transformation coefficients for leads $V_1$, $V_3$, $V_4$, $V_5$, and $V_6$ are determined using the leads I, II, and $V_2$ as base leads. The data for leads $V_1$, $V_3$, $V_4$, $V_5$, and $V_6$ can be collected simultaneously by using five electrodes or can be collected serially by using one electrode and moving it to the appropriate chest positions. In the synthesis mode, only data for the base leads is collected. The data for leads III, a VR, a VL, and a VF are calculated. The data for leads V1, V3, V4, V5, and V6 are synthesized based on the transformation coefficients. The scope of the present invention is defined by the claims that follow.

We claim:

1. A method for synthesizing data for a given lead for an electrocardiogram for a patient, comprising the steps of:
   selecting a plurality of base leads;
   gathering a first set of electrocardiographic data from the patient for the base leads and for the given lead for an interval corresponding to at least one electrocardiographic complex;
   generating a transformation based on the first set of electrocardiographic data;
   gathering a second set of electrocardiographic data from the patient for the base leads for an interval corresponding to at least one electrocardiographic complex; and
   applying the transformation to the second set of electrocardiographic data to effect the synthesis of data for the given lead.

2. The method of claim 1 wherein the step of generating a transformation includes the steps of:
   logically dividing the first set of electrocardiographic data for the base leads and for the given lead into segments; and
   generating a separate transformation for each segment; and wherein the step of applying the transformation includes the steps of:
   logically dividing the second set of electrocardiographic data for the base leads into segments; and
   applying the transformation for each segment to the data in the corresponding segment of the second set of electrocardiographic data to effect the synthesis of the data for the given lead.

3. The method of claim 2 wherein the step of logically dividing the first set of electrocardiographic data into segments and the step of logically dividing the second set of electrocardiographic data into segments divide the electrocardiographic data into three segments defined (1) from the beginning of the electrocardiographic complex to the beginning of the QRS complex, (2) from the beginning of the QRS complex to the ending of the QRS complex, and (3) from the ending of the QRS complex to the ending of the electrocardiographic complex.

4. The method of claim 3 wherein the step of applying the transformation includes the step of adding a dc-offset to the synthesized data to effect the removal inter-segment gaps.

5. The method claim 3 where in the step of applying the transformation includes the step of adjusting the synthesized data so that the mean of the data is equal to zero.

6. The method of claim 3 wherein the base leads are a subset of the 12 standard electrocardiographic leads.

7. The method of claim 6 wherein the subset of the standard electrocardiographic leads includes leads I, II, and $V_2$.

8. The method of claim 2 wherein the step of logically dividing the first set of electrocardiographic data into segments and the step of logically dividing the second set of electrocardiographic data into segments divide the electrocardiographic data into eight segments defined (1) from the beginning of the electrocardiographic complex to the midpoint between the beginning of the electrocardiographic complex and the beginning of the QRS complex, (2) from the midpoint between the beginning of the electrocardiographic complex and the beginning of the QRS complex to the beginning of the QRS complex, (3) from the beginning of the QRS complex to the midpoint between the beginning of the QRS complex and the ending of the QRS complex, (4) from the midpoint between the beginning of the QRS complex and the ending of the QRS complex to the ending of the QRS complex, (5) from the ending of the QRS complex to the point one-fourth the way between the ending of the QRS complex and the ending of the electrocardiographic complex, (6) from the point one-fourth the way between the ending of the QRS complex and the ending of the electrocardiographic complex to the midpoint between the ending of the QRS complex and the ending of the electrocardiographic complex, (7) from the midpoint between the ending of the QRS complex and the ending of the electrocardiographic complex to a point three-fourth the way between the ending of the QRS complex and the ending of the electrocardiographic complex, and (8) from a point three-fourth the way between the ending of the QRS complex and the ending of the electrocardiographic complex to the ending of the electrocardiographic complex.

9. The method of claim 8 wherein the step of applying the transformation includes the step of adding a dc-offset to the synthesized data to effect the removal inter-segment gaps.

10. The method claim 8 where in the step of applying the transformation includes the step of adjusting the synthesized data so that the mean of the data is equal to zero.

11. The method of claim 8 wherein the base leads are a subset of the 12 standard electrocardiographic leads.

12. The method of claim 2 wherein the step of logically dividing the first set of electrocardiographic data into segments and the step of logically dividing the second set of electrocardiographic data into segments includes the steps of: determining time intervals for typical electrocardiographic data for an electrocardiographic complex corresponding to preselected portions of the electrocardiographic complex, and logically dividing the first and second sets of data based on the determined time intervals.

13. The method of claim 12 wherein the step of applying the transformation includes the step of adding a dc-offset to the synthesized data to effect the removal inter-segment gaps.

14. The method claim 12 where in the step of applying the transformation includes the step of adjusting the synthesized data so that the mean of the data is equal to zero.

15. The method of claim 14 wherein the subset of the standard electrocardiographic leads includes leads I, II, and $V_{22}$.

16. The method of claim 2 wherein the step of logically dividing the first set of electrocardiographic data into segments and the step of logically dividing the second set of electrocardiographic data into segments, each set of electrocardiographic data having a QRS compex and an electrocardiographic complex, divides the data into segments such that the data in the QRS complex is in a different segment than the other data comprising the electrocardiographic complex.

17. The method of claims 1, 2, 3, 4, 5, 6, 7, 8, 9, 10, 11, 12, 13, 14, 15 or 16 wherein
the step of generating a transformation includes the step of determining transformation coefficients by applying the equation:

$$B = (ecg^t * ecg)^{-1} * (ecg^t * y)$$

where B represents a vector $(B_1 \ldots B_n)$ such that $B_i$ is the transformation coefficient for base lead i, ecg represents a matrix containing the data from the first set of electrocardiographic data for the base leads, $ecg^t$ represents the transpose of matrix ecg, $^{-1}$ represents matrix inversion, and y is a vector containing the data from the first set of electrocardiographic data for the lead to be synthesized; and
the step of applying the transformation includes the step of determining the synthesized data by applying the equation:

$$y' = B_1 * L_1 + \ldots + B_n * L_n$$

where y' represents a vector containing the synthesized data, $B_i$ represents the transformation coefficient for base lead i, and $L_i$ represents a vector containing the second set of electrocardiographic data for base lead i.

18. The method of claims 1, 2, 3, 4, 5, 6, 7, 8, 9, 10, 11, 12, 13, 14, 15 or 16 wherein
the step of generating a transformation includes the step of determining transformation coefficients by applying the equation:

$$B = (ecg_j^t * ecg_j)^{-1} * (ecg_j^t * y)$$

where B represents a matrix such that $B_{ij}$ is the transformation coefficient for base lead i for the jth order, $ecg_j$ represents a matrix containing a polynomial expression of the data from the first set of electrocardiographic data for the base leads, $ecg_j^t$ represents the transpose of matrix $ecg_j$, $^{-1}$ represents matrix inversion, and y is a matrix containing the data from the first set of electrocardiographic data for the lead to be synthesized; and
the step of applying the transformation includes the step of determining the synthesized data by applying the equation:

$$y' = \sum_{j=1}^{m} \sum_{i=1}^{n} B_{ij} * (L_i)^j$$

where y' represents a vector containing the synthesized data, $B_{ij}$ represents the transformation coefficient for base lead i for the jth order, $L_i$ represents a vector containing the second set of electrocardiographic data for base lead i, n represents the number of base leads, and m represents the order of the polynomial expression.

19. A method for synthesizing data for a given lead for an electrocardiogram for a patient, comprising the steps of:
selecting a plurality of base leads;
gathering a first set of electrocardiographic data from more than one patient for the base leads and for the given lead for an interval corresponding to at least one electrocardiographic complex;
logically dividing the first set of electrocardiographic data for the base leads and for the given lead into segments;
generating a separate transformation for each segment based on the first set of electrocardiographic data;
gathering a second set of electrocardiographic data from the patient for the base leads for an interval corresponding to at least one electrocardiographic complex;
logically dividing the second set of electrocardiographic data for the base leads into segments; and
applying the transformation for each segment to the data in the corresponding segment of the second set of electrocardiographic data to effect the synthesis of data for the given lead.

20. The method of claim 19 wherein the step of logically dividing first set of electrocardiographic data into segments and the step of logically dividing the second set of electrocardiographic data into segments divide the electrocardiographic data into three segments, each set of electrocardiographic data having a beginning of the electrocardiographic complex, a beginning of the QRS complex, an ending of the QRS complex, and an ending of the electrocardiographic complex, the three segments defined (1) from the beginning of the electrocardiographic complex to the beginning of the QRS complex, (2) from the beginning of the QRS complex to the ending of the QRS complex, and (3) from the ending of the QRS complex to the ending of the electrocardiographic complex.

21. The method of claim 19 wherein the step of logically dividing the first set of electrocardiographic data into segments and the step of logically dividing the second set of electrocardiographic data into segments divide the electrocardiographic data into eight segments, each set of electrocardiographic data having a beginning of the electrocardiographic complex, a beginning of the QRS complex, an ending of the QRS complex, and an ending of the electrocardiographic complex, the eight segments defined (1) from the beginning of the electrocardiographic complex to the midpoint between the beginning of the electrocardiographic complex and the beginning of the QRS complex, (2) from the midpoint between the beginning of the electrocardiographic complex and the beginning of the QRS complex to the beginning of the QRS complex, (3) from the beginning of the QRS complex to the midpoint between the beginning of the QRS complex and the ending of the QRS complex, (4) from the midpoint between the beginning of the QRS complex and the ending of the QRS complex to the ending of the QRS complex, (5) from the ending of the QRS complex to the point one-fourth the way between the ending of the QRS complex and the ending of the electrocardiographic complex, (6) from the point one-fourth the way between the ending of the QRS complex and the ending of the electrocardiographic complex to the midpoint between the ending of the QRS complex and the ending of the electrocardiographic complex, (7) from the midpoint between the ending of the QRS complex and the ending of the electrocardiographic complex to a point three-fourth the way between the ending of the QRS complex and the ending of the electrocardiographic complex, and (8) from a point three-fourth the way between the ending of the QRS complex and the ending of the electrocardiographic complex to the ending of the electrocardiographic complex.

22. The method of claim 19 wherein the step of logically dividing the first set of electrocardiographic data into segments and the step of logically dividing the second set of electrocardiographic data into segments divide the data into segments of predetermine lengths corresponding to predetermined time intervals.

23. An apparatus for synthesizing the electrocardiographic data received from an electrode placed on a patient's body surface comprising:
 a first, second, third, and fourth electrode attachable to the body surface, the electrodes responsive to the electrical activity of the heart;
 an analog-to-digital converter operatively connected to the electrodes to convert the electrical signal of the electrodes to digital data;
 data storage means operatively connected to the converter for storing digital data corresponding to an electrocardiographic complex for each electrode;
 calculating means for generating transformation data based on the stored digital data for the first, second, and third electrodes to the fourth electrode; and
 synthesizing means for applying the transformation data to digital data from the first, second, and third electrodes to synthesize data for the fourth electrode.

24. The apparatus of claim 23 additionally comprising segmenting means for dividing the stored digital data into segments.

25. The apparatus of claim 24 wherein the segmenting means divides the stored digital data into three segments, the stored digital data having a beginning of the electrocardiographic complex, a beginning of the QRS complex, an ending of the QRS complex, and an ending of the electrocardiographic complex, the three segments defined (1) from the beginning of the electrocardiographic complex to the beginning of the QRS complex, (2) from the beginning of the QRS complex to the ending of the QRS complex, and (3) from the ending of the QRS complex to the ending of the electrocardiographic complex.

26. The apparatus of claim 24 wherein the segmenting means divides the stored digital data into eight segments, the stored digital data having a beginning of the electrocardiographic complex, a beginning of the QRS complex, an ending of the QRS complex, and an ending of the electrocardiographic complex, the eight segments defined (1) from the beginning of the electrocardiographic complex to the midpoint between the beginning of the electrocardiographic complex and the beginning of the QRS complex, (2) from the midpoint between the beginning of the electrocardiographic complex and the beginning of the QRS complex to the beginning of the QRS complex, (3) from the beginning of the QRS complex to the midpoint between the beginning of the QRS complex and the ending of the QRS complex, (4) from the midpoint between the beginning of the QRS complex and the ending of the QRS complex to the ending of the QRS complex, (5) from the ending of the QRS complex to the point one-fourth the way between the ending of the QRS complex and the ending of the electrocardiographic complex, (6) from the point one-fourth the way between the ending of the QRS complex and the ending of the electrocardiographic complex to the midpoint between the ending of the QRS complex and the ending of the electrocardiographic complex, (7) from the midpoint between the ending of the QRS complex and the ending of the electrocardiographic complex to a point three-fourth the way between the ending of the QRS complex and the ending of the electrocardiographic complex, and (8) from a point three-fourth the way between the ending of the QRS complex and the ending of the electrocardiographic complex to the ending of the electrocardiographic complex.

27. The apparatus of claim 24 wherein the synthesizing means comprises means for adding a dc-offset to the synthesized data to remove inter-segment gaps.

28. The apparatus of claim 24 wherein the synthesizing means comprises means for adjusting the synthesized data so that the means of the data is equal to zero.

29. The apparatus of claims 23, 24, 25, 26, 27, or 28 wherein the transformation data includes transformation coefficients and wherein the calculating means comprises:
 means for determining transformation coefficients by applying the equation:

$$B = (ecg^t * ecg)^{-1} * (ecg^t * y)$$

where B represents a vector $(B_1 \ldots B_n)$ such that $B_i$ is the transformation coefficient for base lead i, ecg represents a matrix containing the data from the first set of electrocardiographic data for the base leads, $ecg^t$ represents the transpose of matrix ecg, $^{-1}$ represents matrix inversion, and y is a vector containing the data from the first set of electrocardiographic data for the lead to be synthesized; and wherein the synthesizing means comprises:
 means for applying the transformation data according to the equation:

$$y' = B_1 * L_1 + \ldots + B_n * L_n$$

where y' represents a vector containing the synthesized data, $B_i$ represents the transformation coefficient for base lead i, and $L_i$ represents a vector containing the second set of electrocardiographic data for base lead i.

* * * * *

UNITED STATES PATENT AND TRADEMARK OFFICE
CERTIFICATE OF CORRECTION

PATENT NO. : 5,058,598

DATED : October 22, 1991

INVENTOR(S) : John M. Nicklas et al.

It is certified that error appears in the above-identified patent and that said Letters Patent is hereby corrected as shown below:

In column 13, claim 15, line 3, please delete "$V_{22}$" and substitute therefor -- $V_2$ --.

Signed and Sealed this

Thirteenth Day of April, 1993

Attest:

STEPHEN G. KUNIN

Attesting Officer

Acting Commissioner of Patents and Trademarks